United States Patent [19]
Scarton et al.

[11] Patent Number: 5,537,862
[45] Date of Patent: * Jul. 23, 1996

[54] QUANTITATIVE METHOD FOR EVALUATION OF THE STATE OF PIANO HAMMER FELT TONAL REGULATION

[75] Inventors: Henry A. Scarton, Troy; Warren C. Kennedy, Feura Bush; John F. Yungman, Delmar, all of N.Y.; Paul N-J. Liang, East Brunswick, N.J.

[73] Assignee: Rensselaer Polytechnic Institute, Troy, N.Y.

[*] Notice: The portion of the term of this patent subsequent to Oct. 5, 2012, has been disclaimed.

[21] Appl. No.: 333,057

[22] Filed: Nov. 1, 1994

Related U.S. Application Data

[62] Division of Ser. No. 957,883, Oct. 5, 1992, Pat. No. 5,423,241.

[51] Int. Cl.⁶ .............................. G01N 3/42; G01N 3/00
[52] U.S. Cl. ..................................................... 73/82; 73/78
[58] Field of Search .............................. 73/12.01, 78, 79, 73/82

[56] References Cited

U.S. PATENT DOCUMENTS

| | | |
|---|---|---|
| 465,505 | 12/1891 | Weser . |
| 3,759,085 | 9/1973 | Wilson et al. ............................. 73/82 |
| 4,034,603 | 7/1977 | Leeb et al. ................................ 73/79 |
| 4,080,863 | 3/1978 | Groeschel ............................. 84/1.27 |
| 4,452,066 | 6/1984 | Klochko et al. ...................... 73/12.01 |
| 4,542,639 | 9/1985 | Cawley et al. ............................ 73/82 |
| 5,079,728 | 1/1992 | Adams et al. ......................... 364/556 |
| 5,423,241 | 6/1995 | Scarton et al. ............................ 73/82 |

Primary Examiner—Richard Chilcot
Assistant Examiner—Max Noori
Attorney, Agent, or Firm—Fish & Richardson

[57] ABSTRACT

A method for measuring dynamic hardness of elastic materials is applied particularly to determining the state of tonal quality for a piano hammer. The method includes selecting a piano hammer of predetermined type from a set of piano hammers, causing the selected piano hammer to strike against an impact surface having the form of a piano string or string grouping appropriate to a piano hammer of the predetermined type, measuring one or more elements of force and motion of the piano hammer striking the impact surface, e.g. force, determining, e.g., the cut-off frequency of the power spectrum for the selected piano hammer striking upon the impact surface, and comparing the determined cut-off frequency of the power spectrum for the selected piano hammer against a predetermined range of cut-off frequencies of power spectrum acceptable for piano hammer of the predetermined type. An apparatus for testing is also described.

4 Claims, 31 Drawing Sheets

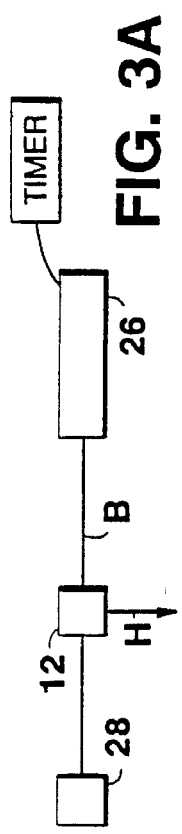
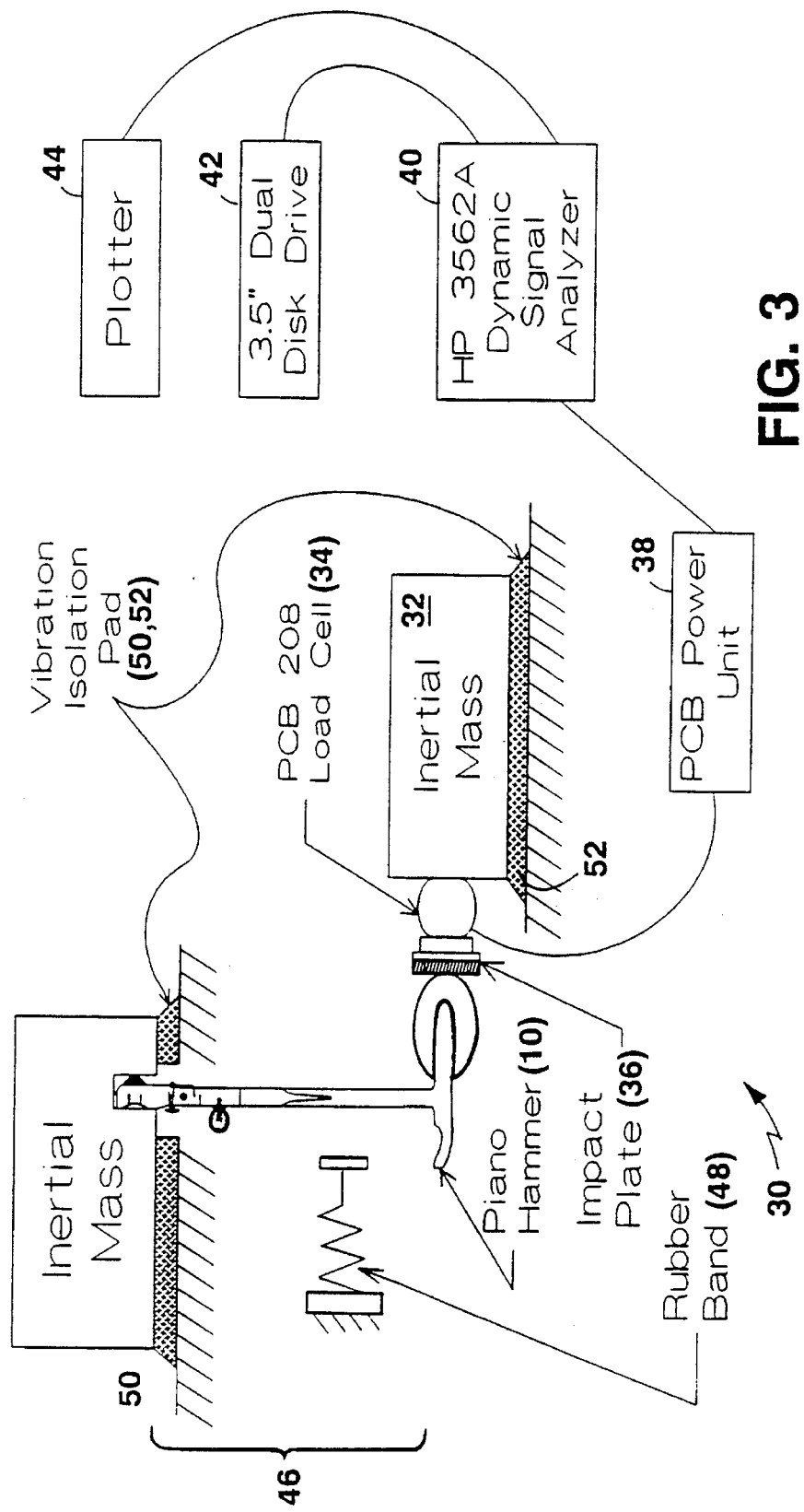

RED VINYL TIP POWER SPECTRUM

BLACK VINYL TIP POWER SPECTRUM

QUANTITATIVE METHOD FOR EVALUATION OF THE STATE OF PIANO HAMMER FELT TONAL REGULATION

This is a divisional of application Ser. No. 07/957,883, filed Oct. 5, 1992 U.S. Pat. No. 5,423,241 patented on Oct. 5, 1993.

BACKGROUND OF THE INVENTION

The invention relates to manufacture and testing of components, namely hammers, for a piano.

Ever since pianos were first developed in the late seventeenth century, manufacture of pianos has been a skilled labor intensive job. As with other jobs performed by skilled craftsmen, "advancement" was slow and the final tone of the finished piano was often strictly dependent upon the ear (hearing) and skill of the craftsman (voicer) involved.

The piano began its history under the name of the pianoforte. This name came from the instrument's unusual ability as a keyed, string instrument to play tones both soft (piano) and loud (forte). The ability to play variations in volume was also one of the main driving forces behind the instrument's development, the other was the increasing desire of the times to play fuller, less delicate music. Many musicians of the time were unsatisfied by the strong, but unemotional, uniform tone produced by the harpsichord in which fairly large strings were plucked by a quill which was controlled by the instrument's keyboard. They were also dissatisfied by the clavichord which produced tone by striking brass hammers against strings and allowed for variations in the volume of play, but was very weak and tinny due to the small thin strings and the brass on steel percussion.

The result of the above dissatisfaction was the invention at about the same time of several different versions of the pianoforte. The most widely acknowledged successful version was a pianoforte developed by Bartolomo Christofori who published details of the instrument in 1711 and completed a prototype around 1720. Among the important innovations contained in Christofori's pianoforte were the hammers which were wooden blocks covered on the striking surface with soft leather.

Christofori's first compliant piano hammer was simply a polygonal block of wood covered with soft leather on the striking surface as is illustrated in FIG. 1. The hammer was improved over the next several years with the shape being changed to a wedge shaped piece of wood over the thin end of which a piece of leather was bent and attached to give the piano hammer the same basic shape that it has today. Two layers of leather were used in this design with the inner layer being a firm sole leather, and the outer layer being a softer sheepskin. The final manifestation of the leather covered piano hammer used three layers of leather of varying firmness with the softest leather on the outside and the firmest layer on the inside. All of these attempts were aimed toward providing a piano hammer that was soft and compliant at the surface to provide excellent tone for pianissimo playing while the hammer was firmer underneath to provide the strength for forte playing.

After the invention of the iron frame for the strings on a piano, heavier strings could be used at higher tensions to produce a fuller sound from the piano. This rendered the leather covered piano hammer unacceptable. The result was the development and patenting of a felt covered piano hammer by Alpeus Babcock in 1833. These hammers provided a more acceptable tone than the previously discussed leather covered hammers and gained popularity, thus spurring the development of the felt industry and producing patents for the first machine made felt. Felt is a fabric that is formed of hair and/or wool whose fibers are encouraged to interlace through the use of heat, moisture, rolling, beating and pressure. Felt manufacturers experimented with different raw materials and eventually settled on the wool from the merino sheep of Cape Colony in Africa which remained the hammer felt of choice for many years. Eventually, machines were invented to cover the raw wood piano hammers with felt. But, the process of fine tuning the tone of the piano by adjusting the hardness of the hammer felt has remained a skilled craft even to today. This process of tonally regulating the piano hammers is commonly called voicing. It is one of the final steps in the manufacture of a piano, and it is also one of the more time consuming operations.

After the initial step of making sure that the piano hammer felt is properly shaped for the hammer in question, particularly that it is flat across the width of the striking surface, the voicer (a person performing the tonal regulation) typically plays all the notes on the piano several times at varying volume levels to judge the overall tone of the instrument. While doing this the voicer also listens for individual notes which stand out as being too soft (producing a muted or mushy sound) or notes which appear to be too hard (producing an excessively loud or tinny sound).

The voicer adjusts the tone of a hammer that sounds too soft by applying a solution of lacquer and lacquer thinner to the shoulders of the hammer felt of a modern piano hammer, e.g. as shown in FIG. 2 and also as described in Lombino U.S. Pat. No. , issued , 1992 (Ser. No. 07/657,882, filed Feb. 19, 1991), the disclosure of which is incorporated herein by reference. The shoulder of the hammer is the portion of the hammer adjacent to the striking surface. A method used to harden the striking surface is to iron the surface of the felt with a steam iron and thus encourage the felt fibers to intertwine themselves more tightly.

Hammers that appear to be too hard are adjusted by the voicer through the use of needles (usually three needles oriented axially in the end of a holder) in a process called needling. In order to properly needle the piano hammer felt, the voicer determines whether the hammer is too hard overall, or just at specific volume levels. If the hammer is too hard at very soft (pianissimo) levels, the voicer lightly needles the striking surface of the hammer to a depth of one to two millimeters. However, if the hammer appears too hard at forte or greater levels, then the shoulders of the hammer are deep needled. Where to deep needle the shoulders of the hammer also depends on the volume at which the tone is being adjusted, with the louder volumes causing the needling to be done further away from the striking surface.

SUMMARY OF THE INVENTION

According to one aspect of the invention, a method for determining the state of tonal quality for a piano hammer comprises selecting a piano hammer of predetermined type from a set of piano hammers, causing the selected piano hammer to strike against a rigidly mounted impact surface having the form of a piano string or string grouping appropriate to a piano hammer of the predetermined type, measuring the force of the piano hammer striking the impact surface, determining the cut-off frequency of the power spectrum for the selected piano hammer striking upon the impact surface, and comparing the determined cut-off frequency of the power spectrum for the selected piano hammer against a predetermined range of cut-off frequencies of power spectrum acceptable for piano hammer of the predetermined type.

Preferred embodiments of this aspect of the invention may include one or more of the following features. The method comprises the further step of providing a test apparatus comprising a frame for pivotable mounting of a piano hammer to be tested, and an impact target positioned to be struck with force by a piano hammer pivotably mounted upon the frame, the impact surface having a form replicating that of a piano string or a grouping of piano strings appropriate to a piano hammer to be tested. The method comprises the further step of providing a test apparatus comprising a frame for mounting of a piano hammer to be tested and an impact target, the piano hammer and the impact target positioned in manner for striking contact with force therebetween, the impact surface having a form replicating that of a piano string or a grouping of piano strings appropriate to a piano hammer to be tested. The method comprises the further step of establishing a predetermined range of acceptable impact velocity, measuring the impact velocity of the selected piano hammer, and, when determining the cut-off frequency of the power spectrum for the selected piano hammer striking upon the impact surface, considering only data for instances when the measured impact velocity is within the established range.

According to another aspect of the invention, a method for determining the state of tonal quality for a piano hammer comprises selecting a piano hammer of predetermined type from a set of piano hammers, causing the selected piano hammer to strike against a rigidly mounted impact surface having the form of a piano string or string grouping appropriate to a piano hammer of the predetermined type, measuring the force of the piano hammer striking the impact surface, measuring the impact velocity of the selected piano hammer, and, determining the cut-off frequency of the power spectrum for the selected piano hammer striking upon the impact surface, and comparing the determined cut-off frequency of the power spectrum for the selected piano hammer against a predetermined range of cut-off frequencies of power spectrum acceptable for piano hammer of the predetermined type.

According to yet another aspect of the invention, a method for determining the state of tonal quality for a piano hammer comprises selecting a piano hammer of predetermined type from a set of piano hammers, causing the selected piano hammer to strike against a rigidly mounted impact surface having the form of a piano string or string grouping appropriate to a piano hammer of the predetermined type, measuring the force of the piano hammer striking the impact surface, measuring the impact velocity of the selected piano hammer, and, comparing the slope of force versus impact velocity for the selected piano hammer against the slope of force versus impact velocity acceptable for a piano hammer of the predetermined type.

According to another aspect of the method of the invention, a method for determining the state of tonal quality for a piano hammer comprising selecting a piano hammer of predetermined type from a set of piano hammers, causing the selected piano hammer to strike against a rigidly mounted impact surface having the form of a piano string or string grouping appropriate to a piano hammer of the predetermined type, measuring one or more elements of force and motion of the piano hammer and the impact surface, and comparing the one or more elements against a predetermined range of elements acceptable for a piano hammer of the predetermined type.

In preferred embodiments of each aspect described, the material of the impact surface is selected to be harder than the material of the piano hammer to be tested.

According to another aspect of the invention, an apparatus for determining the state of tonal quality for a piano hammer comprises a frame adapted to provide a pivotable mount for a piano hammer to be tested and an impact target, the piano hammer and the impact target positioned upon the frame in manner for striking contact with force therebetween, the impact surface having a form replicating that of a piano string or a grouping of piano strings appropriate to a piano hammer to be tested, sensing means for sensing the striking force between the piano hammer and the impact surface, and determining means associated with the sensing means for determining the cut-off frequency of the power spectrum for the piano hammer striking upon the impact surface.

According to another aspect of the apparatus of the invention, as apparatus for determining the state of tonal quality for a piano hammer comprises a frame adapted to provide a mount for a piano hammer to be tested, an impact target positioned to be struck with force by a piano hammer pivotably mounted upon the frame, the impact surface having a form replicating that of a piano string or a grouping of piano strings appropriate to a piano hammer to be tested, sensing means associated with the impact surface for sensing the striking force of a piano hammer upon the impact surface, and determining means associated with the sensing means for determining the cut-off frequency of the power spectrum for the piano hammer striking upon the impact surface.

Preferred embodiments of these aspect of the invention may include one or more of the following features. The frame comprises a significant inertial mass compared to the mass of the piano hammer. Preferably, the frame further comprises means for isolating the piano hammer from external vibration. The impact target comprises a significant inertial mass compared to the mass of the piano hammer. Preferably, the impact target comprises means for isolating the impact surface from external vibration. The apparatus further comprises timing means for determining the impact velocity of a piano hammer during testing. Preferably, the timing means comprises a laser light source at one side of a path of travel for a piano hammer, or set of piano hammers, being tested, the laser light source adapted to emit a beam across the path of travel, a photo transistor at an opposite side of the path of travel and adapted to detect the beam, and a timer connected to the photo transistor and adapted to measure a period of time during which detection of the beam is interrupted by passage of a piano hammer. The apparatus further comprises means for motivating a piano hammer mounted upon the frame toward striking impact upon the surface of the impact target. The apparatus further comprises means for motivating the impact target mounted upon the frame toward striking impact with a surface of piano hammer. The material of the impact surface is selected to be harder than the material of the piano hammer to be tested.

According to another aspect of the invention, an apparatus for determining the state of tonal quality for a piano hammer comprises a frame adapted to provide a mount for a piano hammer to be tested, an impact target positioned to be struck with force by a piano hammer pivotably mounted upon the frame, the impact surface having a form replicating that of a piano string or a grouping of piano strings appropriate to a piano hammer to be tested, and sensing means associated with the impact surface for sensing one or more elements of force and motion of the piano hammer and the impact surface.

According to yet another aspect of the invention, a method for measuring the dynamic hardness of elastic materials comprises causing impact between a test element of elastic material and an impact surface, measuring the striking force between the test element and the impact surface, and determining the cut-off frequency of the power spectrum for the impact of the test element with the impact surface.

According to another aspect of this invention, a method for measuring the dynamic hardness of elastic materials comprises causing impact between a test element of elastic material and an impact surface, measuring the striking force between the test element and the impact surface, and measuring the relative impact velocity of between the test element and the impact surface.

Preferred embodiments of this aspect of the invention may include one or more of the following features. The method comprises the further step of determining the slope of force versus impact velocity. The method comprises the further steps of determining the cut-off frequency of the power spectrum for the impact of the test element with the impact surface, and determining the slope of cut-off frequency versus impact velocity. The impact surface is rigidly mounted and the method further comprises striking the test element against the impact surface. The method comprises the further step of providing a test apparatus comprising a frame for pivotable mounting of a test element to be tested, and an impact target positioned to be struck with force by a test element pivotably mounted upon the frame. The method comprises the further step of establishing a predetermined range of acceptable impact velocity, measuring the impact velocity of the test element, and, when determining the cut-off frequency of the power spectrum for the test element striking upon the impact target, considering only data for instances when the measured impact velocity is within the established range.

According to another aspect of the invention, a method for measuring the dynamic hardness of elastic materials comprises causing impact between a test element of elastic material and an impact surface, measuring one or more elements of force and motion between the test element and the impact surface.

According to the method of the invention, compliance of a piano hammer felt is determined by studying the Power Spectrum of the Force versus Time data for impact of a piano hammer which is struck against a rigidly mounted load cell to which an impact plate, constructed as an exact replica of a piano string grouping, is attached.

In preferred embodiments of the invention, load cells for treble strings are constructed by attaching three pieces of piano wire to the load cell face plate; impact plates for the lower mid-range and bass notes are constructed by attaching an epoxy model of the appropriate strings to the face plate.6

The method provides for accurate prediction of the shape of the roll-off of the partials in the piano string while being much simpler than methods which require instrumentation of the hammer and/or string, and methods which include or model the flexible interface between the hammer and the string.

According to another aspect of the invention, a method for measurement of the hardness of elastic materials provides an accurate dynamic hardness measurement.

Objectives of the invention include providing means for quantitative, accurate and repeatable determination of the state of tonal regulation or voice of a piano hammer, including means for recording and analyzing a given signal with the intent of reducing the possibility of error in the transcription of the information contained therein to other people. Also, to provide a less time consuming process and more consistent product; in particular, to address the process of tonal regulation of piano hammers by providing a quantitative measurement technique. The resulting method is substantially more quantitative than methods presently used during regulation of a piano action in industry in which the number of harmonics (partials) introduced when striking a piano string by a piano hammer are compared aurally to known standards based upon the experience of the tonal regulator.

These and other features and advantages of the invention will be seen from the following description of a presently preferred embodiment, and from the claims.

DESCRIPTION OF PRESENTLY PREFERRED EMBODIMENTS

We first briefly describe the drawings.

FIG. 3 is a similar representation of a test apparatus of the invention, while FIG. 3A is a top sectional representation of the timing apparatus for a single hammer and FIG. 3B is a schematic representation of the timing apparatus for a piano keyboard;

FIGS. 24d–24f being plan, top and side views, respectively, of a two string configuration; and FIGS. 24g–24i being plan, top and side views, respectively, of a typical one string configuration;

Figure 1:
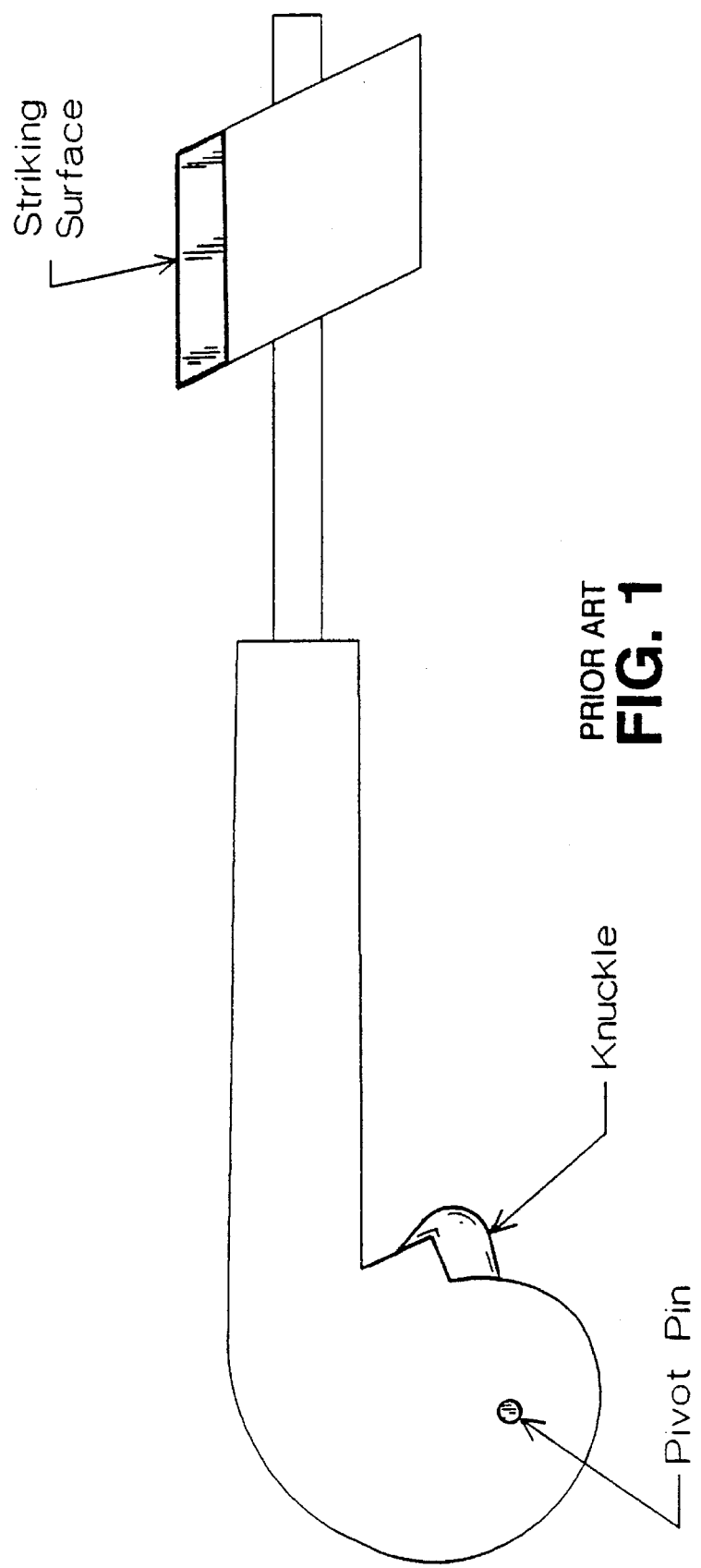
FIG. 1 is a somewhat diagrammatic representation of a Christofori piano hammer.

The invention relates to a method and apparatus for measuring the effects of the hardness of the piano hammer felt on the tone of the piano. The airborne acoustic signal studied was from a Steinway & Sons, Model M, small grand piano. It is known that characteristics of the vibration created by two impacting objects depends on several factors.

These include the relative velocity of the two objects, the mass of the objects, the hardness of the objects, the profile of the objects where they impact each other, the resonant structure of the objects, and any damping that is present during the collision. Several of these factors have been fixed through the years of development of pianos and are not considered herein. These factors include the hardness of the piano strings, the profile of the strings, and the resonant structure of the strings and hammers.

However, the hardness of the hammer felt where the hammer hits the string may be measured quantitatively. The harder the hammer, the more overtones or partials that can be excited in a string. (It is not necessary to excite the string in order to evaluate the exciter, that is, the piano hammer and the felt used on those hammers.)

In order to accurately perform the study of the piano hammer hardness, several factors must be considered. One of the factors discussed above is the velocity of the hammer just before impact which affects the Force versus Time curve of the hammer impact, and thus the number of partials excited in the struck string. For example, it will be shown that for voiced piano hammer #88, the cut-off frequency (as defined below) increases by 1800 hertz as velocity increases from 40 inches per second to 130 inches per second (1.01 meters per second to 3.30 meters per second). Therefore, this factor must be precisely measured and controlled (e.g., by determining how far to pull the hammer back against the rubber band used for providing motivating force in the testing apparatus). The velocity measurement was performed through use of a laser light 26 and a photo transistor 28. When the beam (B) between the source and the detector was interrupted by passage of the hammershank 12, a timer counted the amount of time of the interruption by the hammershank. Since all of the Steinway & Son piano hammershanks tested have a known diameter of 0.240 inch (6.096 mm) at the point where the beam strikes the shank, the average velocity over a very short period of time (e.g., for these tests, a maximum of 5 milliseconds) can be calculated.

The other factor accounted for in this testing was the profile of the piano strings used for each of the keys. Each piano string has a specific profile, which was found to have an effect upon the exact shape of the Force versus Time data. In order to account for this factor, impact plates representative of string profile were constructed and attached to a load cell on the impacted surface. These impact plates thus varied in construction depending upon the piano hammers for which they were to be used. The configuration and construction of these impact plates is discussed below.

It was shown that the cut-off frequency of a piano hammer from the bass range is 400 hertz higher when striking a flat plate than when striking an impact plate shaped like the piano strings. The results for a piano hammer in the treble range show an even greater increase of 1000 hertz when struck against a flat plate instead of a impact plate simulating the appropriate strings.

Figure 3B:
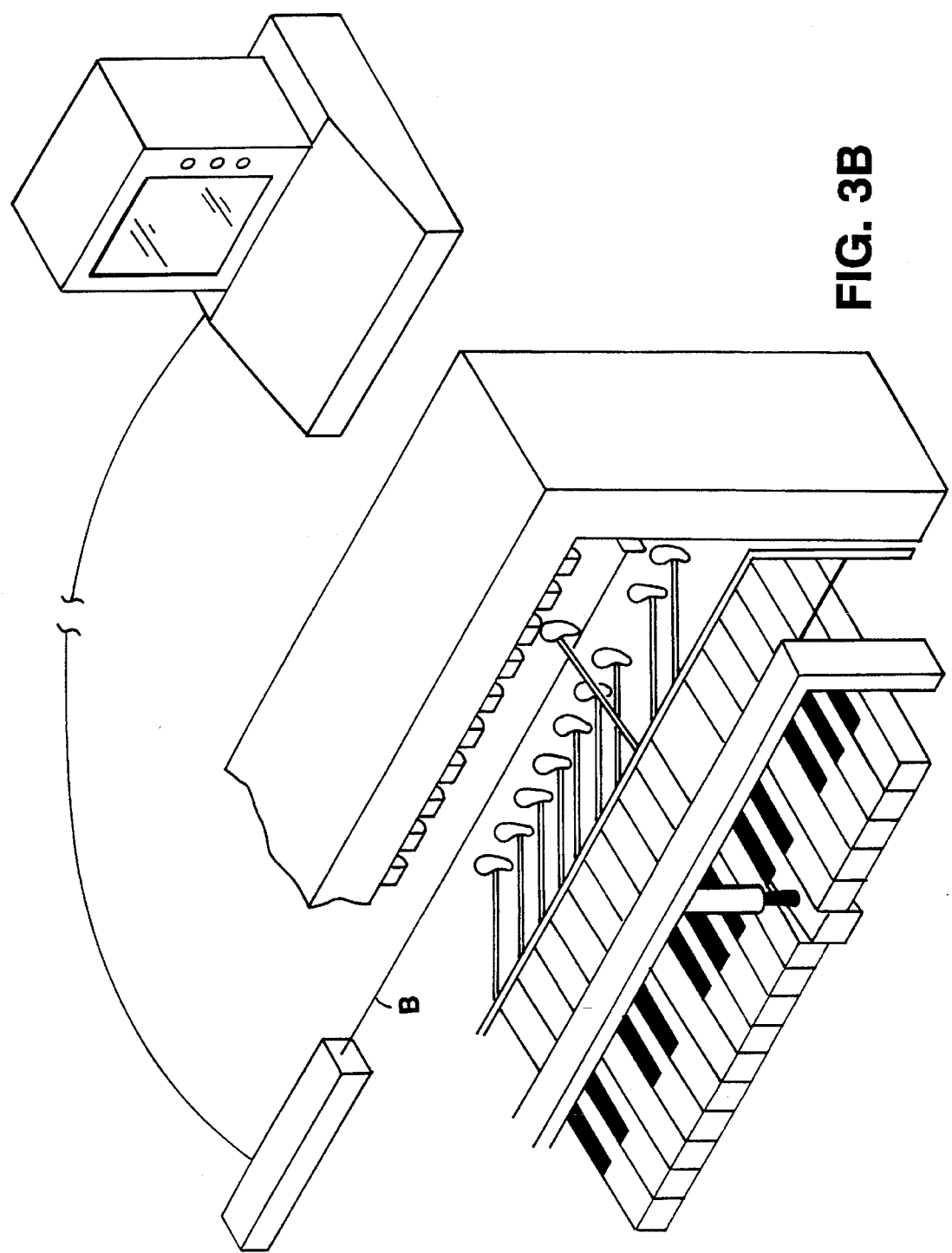

Referring now to FIG. 3, in order to ensure proper alignment of the piano hammers with the load cell and impact plate, a groove was machined into the test apparatus. The groove was slightly larger than the width of the hammershank flange and contained a stud set at a predetermined height so that the head of the hammer was aligned vertically as well as horizontally.

As has been previously stated, the main topic of interest was the piano hammer felt. Since felt is absorptive and can change properties during testing, humidity and temperature conditions were recorded during all testing. Testing occurred in the winter time when the average conditions were 72° F. and 32% relative humidity. Although conditions varied, experiments performed by Anders Askenfelt of Sweden showed that the influence of humidity on piano hammer felt is rather insignificant.

The tests were conducted with one set of new, completely voiced piano hammers from a Model L grand piano and one set of new, unvoiced hammers, also for a Model L grand piano (both provided by Steinway & Sons, Long Island City, N.Y.). As will be shown, the process of voicing a piano hammer can increase the cut-off frequency by 250 hertz or more for piano hammers in the bass range and by 500 hertz or more for hammers in the treble range.

Once both sets of hammers were tested, airborne acoustical recordings were also made of several voiced hammers striking the appropriate strings in the new Model M grand piano (also supplied by Steinway & Sons). Using the Power Spectrum of these airborne acoustical recordings, the number of partials excited in the strings was found by counting the number of spectral peaks and compared against the number of partials calculated (described in more detail below) from the cut-off frequency measured in the hammer tests which did not take into account the compliance of the strings. This comparison showed that the compliance of the strings was not a necessary factor for determination of the state of tonal regulation of the piano hammer felt.

A partial is a component of a sound sensation which may be distinguished as a simple sound that cannot be further analyzed by the ear and which contributes to the character of the complex tone or complex sound. It is a genuine part of the complete sound. The fundamental frequency of the string is the frequency of the first partial, or that frequency caused by the piano string vibrating in the first mode, or the lowest natural frequency of free vibration of the string. A harmonic is a partial whose frequency is usually an integral multiple of the frequency of the first partial or fundamental frequency of the string.

Figure 2:
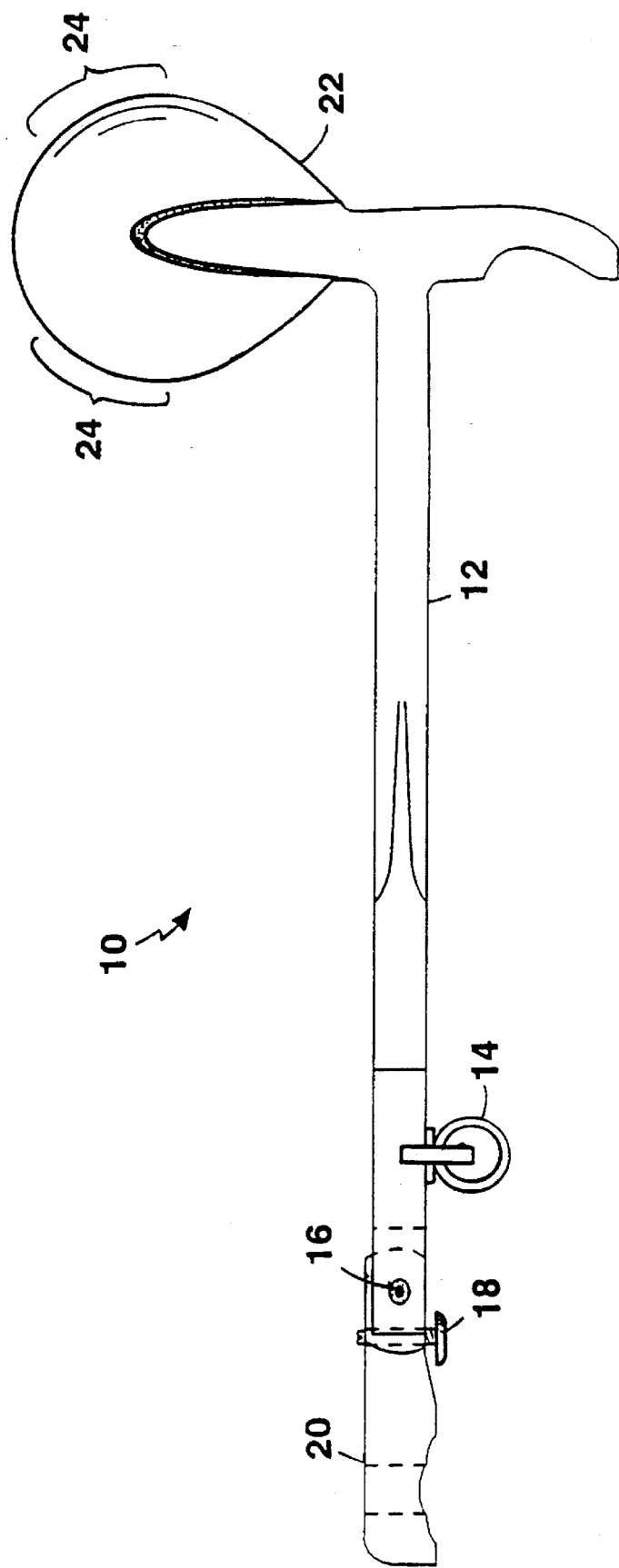
FIG. 2 is a similar representation of a modern piano hammer assembly.

Referring now to FIG. 2, a typical piano hammer 10 includes a hammershank 12 engaged upon a knuckle 14 and mounted to pivot on pivot pin 16, and attached by drop screw 18 to hammershank flange 20. The focus of this discussion is upon the hammer felt 22 having shoulder regions 24.

Musical expressions for volume level include "piano" which means soft or quiet, and "forte" which means loud. The word "mezzo" means medium or middle volume level, and it is often used in combination with "piano" and "forte" e.g. the phrase "mezzo piano" means slightly louder than "piano", and "mezzo forte" means slightly softer than "forte". Also, "pianissimo" means very quietly, and "fortissimo" means very loudly.

There are two basic musical scales in western music. The first is the scale of Just Intonation which is based on the fact that tones with frequencies related by certain ratios of small integers are pleasing to the ear. The basic frequency ratio of 2:1 is called an octave and is further divided into 16 steps based on an integer ratio from a starting point. These ratios are shown in Table 1. Since the actual spacing between these steps is not consistent, the frequency of a given note depends upon the initial note chosen and the problem this causes with a fixed intonation instrument such as a piano can be seen.

TABLE 1

Scale of Just Intonation

| Interval Name | Frequency ratio from starting point | Frequency Multiple from starting point |
|---|---|---|
| Unison | 1:1 | 1 |
| Semitone | 16:15 | 1.0667 |
| Minor Tone | 10:9 | 1.1111 |
| Major Tone | 9:8 | 1.125 |
| Minor Third | 6:5 | 1.2 |
| Major Third | 5:4 | 1.25 |
| Perfect Fourth | 4:3 | 1.3333 |
| Augmented Fourth | 45:32 | 1.4063 |
| Diminished Fourth | 64:45 | 1.4222 |
| Perfect Fifth | 3:2 | 1.5 |
| Minor Sixth | 8:5 | 1.6 |
| Major Sixth | 5:3 | 1.6667 |
| Harmonic Minor Seventh | 7:4 | 1.75 |
| Grave Minor Seventh | 16:9 | 1.7778 |
| Minor Seventh | 9:5 | 1.8 |
| Major Seventh | 15:8 | 1.875 |
| Octave | 2:1 | 2 |

The second, and now generally accepted, scale is the scale of Equal Temperament. This scale defines an octave the same way as the scale of Just Intonation, that is, a frequency ratio of 2:1. However, the octave is then divided into 12 equal steps, each being in the ratio of the twelfth root of two ($2^{1/12}$) to one with the consecutive tones as is shown in Table 2. As any two consecutive tones are in the same ratio, it does not matter what note is the starting note for the scale. This consistency is the reason that pianos are tuned to the scale of Equal Temperament. It may be noted here that since the ear more naturally follows the scale of Just Intonation, the player of a variable pitched instrument such as the violin will gravitate towards this scale when playing unaccompanied for long periods of time. However, when joined by a piano accompaniment, the violinist will automatically revert to the scale of Equal Temperament to remain in tune with the piano.

TABLE 2

Scale of Equal Temperament

| Interval Name | Frequency ratio from starting point | Frequency Multiple from starting point |
|---|---|---|
| Unison | 1:1 | 1 |
| Semitone | $2^{1/12}$:1 | 1.0595 |
| Whole Tone | $2^{2/12}$:1 | 1.1225 |
| Minor Third | $2^{3/12}$:1 | 1.1892 |
| Major Third | $2^{4/12}$:1 | 1.2599 |
| Perfect Fourth | $2^{5/12}$:1 | 1.3348 |
| Augmented Fourth | $2^{6/12}$:1 | 1.4142 |
| Perfect Fifth | $2^{7/12}$:1 | 1.4983 |
| Minor Sixth | $2^{8/12}$:1 | 1.5874 |
| Major Sixth | $2^{9/12}$:1 | 1.6818 |
| Minor Seventh | $2^{10/12}$:1 | 1.7818 |
| Major Seventh | $2^{11/12}$:1 | 1.8877 |
| Octave | 2:1 | 2 |

The frequencies for all the notes on a piano, as tuned to the scale of Equal Temperament, are shown in Table 3 along with the nomenclature for each note. The subscript in the note name refers to the octave of the note with zero being the lowest octave. (This notation was suggested in a paper written by Robert W. Young in 1939 because $C_O$ is then 16.352 hertz which is approximately the lowest frequency audible to a healthy human ear. The "#" is a sharp indication which means the frequency played one semitone above the note named.

TABLE 3

Piano String Frequencies

| Hammer or Key Number | Fundamental Frequency (Hz) | Note |
|---|---|---|
| 1 | 27.500 | $A_0$ |
| 2 | 29.135 | $A^\#_0$ |
| 3 | 30.868 | $B_0$ |
| 4 | 32.703 | $C_1$ |
| 5 | 34.648 | $C^\#_1$ |
| 6 | 36.708 | $D_1$ |
| 7 | 38.891 | $D^\#_1$ |
| 8 | 41.203 | $E_1$ |
| 9 | 43.654 | $F_1$ |
| 10 | 46.249 | $F^\#_1$ |
| 11 | 48.999 | $G_1$ |
| 12 | 51.913 | $G^\#_1$ |
| 13 | 55.000 | $A_1$ |
| 14 | 58.270 | $A^\#_1$ |
| 15 | 61.735 | $B_1$ |
| 16 | 65.406 | $C_2$ |
| 17 | 69.296 | $C^\#_2$ |
| 18 | 73.416 | $D_2$ |
| 19 | 77.782 | $D^\#_2$ |
| 20 | 82.407 | $E_2$ |
| 21 | 87.307 | $F_2$ |
| 22 | 92.499 | $F^\#_2$ |
| 23 | 97.999 | $G_2$ |
| 24 | 103.83 | $G^\#_2$ |
| 25 | 110.00 | $A_2$ |
| 26 | 116.54 | $A^\#_2$ |
| 27 | 123.47 | $B_2$ |
| 28 | 130.81 | $C_3$ |
| 29 | 138.59 | $C^\#_3$ |
| 30 | 146.83 | $D_3$ |
| 31 | 155.56 | $D^\#_3$ |
| 32 | 164.81 | $E_3$ |
| 33 | 174.61 | $F_3$ |
| 34 | 185.00 | $F^\#_3$ |
| 35 | 196.00 | $G_3$ |
| 36 | 207.65 | $G^\#_3$ |

TABLE 3-continued

Piano String Frequencies

| Hammer or Key Number | Fundamental Frequency (Hz) | Note |
|---|---|---|
| 37 | 220.00 | $A_3$ |
| 38 | 233.08 | $A^\#_3$ |
| 39 | 246.94 | $B_3$ |
| 40 | 261.63 | $C_4$ |
| 41 | 277.18 | $C^\#_4$ |
| 42 | 293.66 | $D_4$ |
| 43 | 311.13 | $D^\#_4$ |
| 44 | 329.63 | $E_4$ |
| 45 | 349.23 | $F_4$ |
| 46 | 369.99 | $F^\#_4$ |
| 47 | 391.99 | $G_4$ |
| 48 | 415.31 | $G^\#_4$ |
| 49 | 440.00 | $A_4$ |
| 50 | 466.16 | $A^\#_4$ |
| 51 | 493.88 | $B_4$ |
| 52 | 523.25 | $C_5$ |
| 53 | 554.37 | $C^\#_5$ |
| 54 | 587.33 | $D_5$ |
| 55 | 622.25 | $D^\#_5$ |
| 56 | 659.26 | $E_5$ |
| 57 | 698.46 | $F_5$ |
| 58 | 739.99 | $F^\#_5$ |
| 59 | 783.99 | $G_5$ |
| 60 | 830.61 | $G^\#_5$ |
| 61 | 880.00 | $A_5$ |
| 62 | 932.33 | $A^\#_5$ |
| 63 | 987.77 | $B_5$ |
| 64 | 1046.5 | $C_6$ |
| 65 | 1108.7 | $C^\#_6$ |
| 66 | 1174.7 | $D_6$ |
| 67 | 1244.5 | $D^\#_6$ |
| 68 | 1318.5 | $E_6$ |
| 69 | 1396.9 | $F_6$ |
| 70 | 1475.0 | $F^\#_6$ |
| 71 | 1568.0 | $G_6$ |
| 72 | 1661.2 | $G^\#_6$ |
| 73 | 1760.0 | $A_6$ |
| 74 | 1864.7 | $A^\#_6$ |
| 75 | 1975.5 | $B_6$ |
| 76 | 2093.0 | $C_7$ |
| 77 | 2217.4 | $C^\#_7$ |
| 78 | 2349.3 | $D_7$ |
| 79 | 2489.0 | $D^\#_7$ |
| 80 | 2637.0 | $E_7$ |
| 81 | 2793.8 | $F_7$ |
| 82 | 2959.9 | $F^\#_7$ |
| 83 | 3136.0 | $G_7$ |
| 84 | 3322.4 | $G^\#_7$ |
| 85 | 3520.0 | $A_7$ |
| 86 | 3729.3 | $A^\#_7$ |
| 87 | 3951.1 | $B_7$ |
| 88 | 4186.0 | $C_8$ |

Experimental Method

Equipment

The following is a description of the equipment used for the experimentation.

Hewlett Packard model 3562A Dynamic Signal Analyzer, serial number 2435A00275; Including Hewlett Packard Dual 3.5" Disk, Drive model 9122D, serial number 2518A40463 and Hewlett Packard Plotter model 7470A, serial number 2308A97959.

PCB Piezotronics model 208A02 Force Transducer, serial number 7805, with calibrated range of 0 to 100 pounds and resolution of 0.002 pounds (purchased from PCB Piezotronics, New York).

PCB Piezotronics model 480D06 Power Unit, serial number 6129.

Uniphase model 1508-0 0.95 milliwatt, Helium Neon Gas Laser, serial number 430386 (purchased from Edmund Scientific Company, New Jersey).

Brüel and Kjaer type 213H Sound Level Meter, serial number 598527.

Equipment Set-Up

The test apparatus 30, shown in FIG. 3, consists of a 121.5 pound (540.4 newtons) block of steel 32 which is shown in the schematic as the inertial mass to which a force transducer 34 is attached. The mass of the steel block was chosen this large (three orders of magnitude larger than that of a piano hammer which weighs approximately 0.529 ounce (0.033 pound or 0.147 newton)) to ensure that any vibration induced by the impact of the piano hammer 10 would be extremely small in amplitude. Attached to the face of the transducer was an impact plate 36 which was made to simulate the shape of the piano string or group of strings that each hammer hits in the piano. This impact plate was changed as necessary when the hammers were changed in order to ensure that each hammer was striking the appropriate profile. The configuration and construction of the individual impact plates is discussed below.

Comparisons were made between hammers striking a flat plate versus a contoured impact plate. The shift in cut-off frequency was found to be substantial and is further discussed below.

The force transducer was connected to a PCB power unit 38 and the gain on the power unit was set to one. The output of the power unit was then connected to Input Channel 1 of a signal analyzer 40. The signal analyzer was connected to a dual disk drive 42 for storage of information and to a plotter 44 for printing of the acquired data curves.

A frame 46 was built to hold the piano hammer 10 at the proper position with respect to the impact plate 36 of the transducer 34. This frame was also massive (62 pounds or 275.8 newtons) to reduce the amplitude of sympathetic vibrations which may be caused by the piano hammer impacting the force transducer. Included in this frame were the connection points for a rubber band 48. This rubber band was used to supply the piano hammer with the motivating force normally provided by a human finger striking a piano key. Both the frame and the inertial mass were set on vibration isolation pads 50, 52 to protect them from environmental vibrations, as well as to prevent any vibration from being transmitted between them.

Referring to FIG. 3A, the final element of the physical set-up was the timing mechanism. This was provided by setting a laser light source 26 with the laser beam (B) perpendicular to the piano hammer 12 path of travel (arrow H). A photo transistor 28 was placed on the other side of the piano hammer and connected to the timing circuit. This arrangement is described in more detail below.

Signal Analyzer Set-Up

Figure 4:
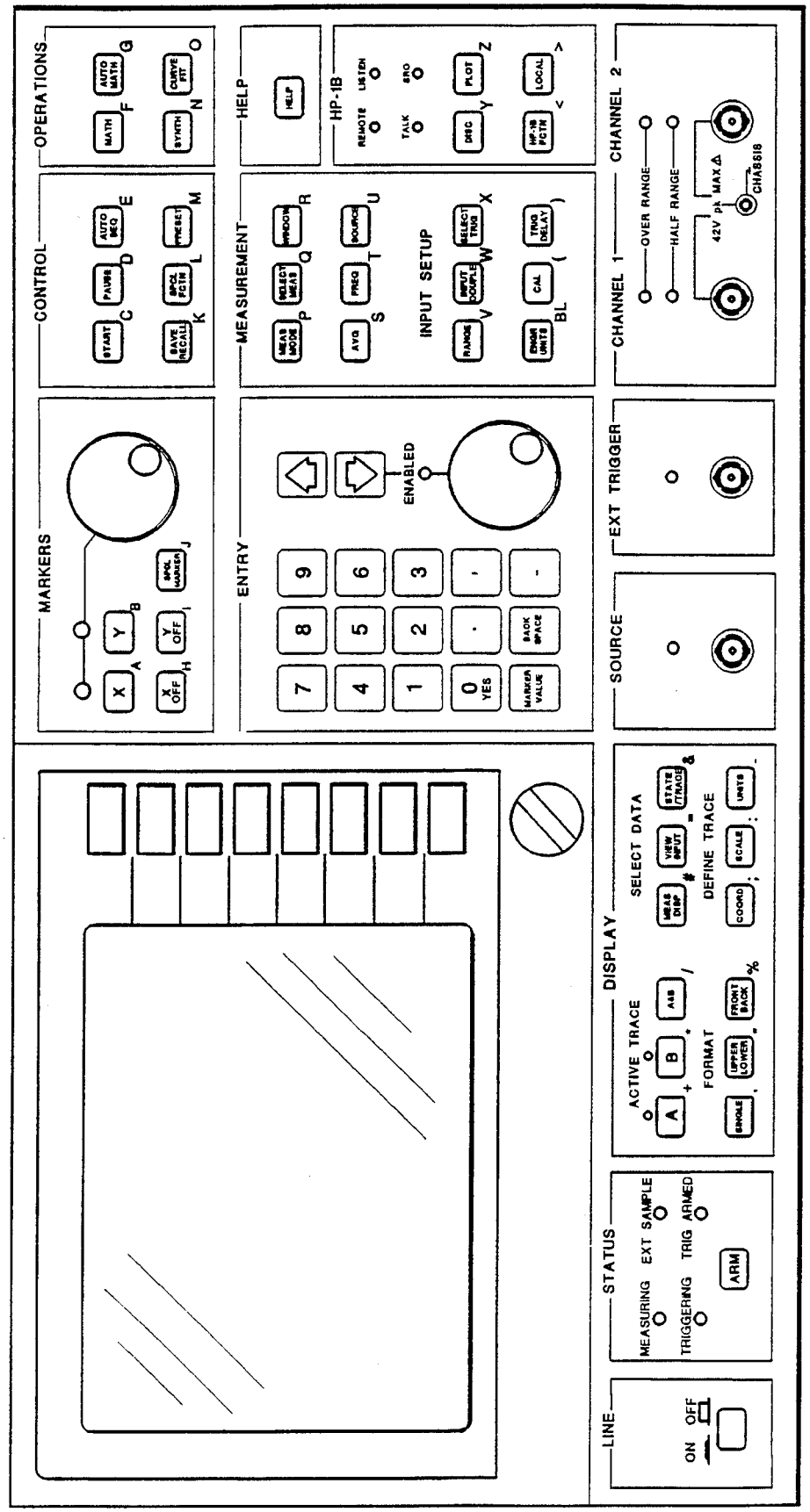
FIG. 4 is a face view of the panel of a representative signal analyzer.

Referring now to FIG. 4, the signal analyzer 40 (HP3562A) was set-up by performing the keystrokes described below (note that soft key labels appear on the right side of the display screen of the HP 3562A):

> SPCL FCTN key; Date (M,D,Y) soft key to set date, Time (H,M,S) soft key to set time.

> MEAS MODE key; Linear Res soft key.

> SELECT MEAS key; Power Spec soft key, Ch 1 Active soft Key.

> WINDOW key; Force/Expon soft key, Force Chan 1 soft key.

> AVG key; Stable (Mean) soft key, Number Avgs soft key, 3, Enter soft key, Tim Av soft key (set time averaging to on), Next soft key, Manual Preview soft key.
> FREQ key; Center Freq soft key, 5, kHz soft key, Freq Span soft key, 10, kHz soft key.
> SOURCE key; Source Off soft key.
> RANGE key; Chan 1 Range soft key, 4, V soft key.
> INPUT COUPLE key; Chan 1 AC/DC soft key (set input couple to DC), Float Chan 1 soft key.
> SELECT TRIG key; Chan 1 Input soft key, Trig Level soft key, 153, mV soft key, Arm Au/Man soft key (set to Au for automatic arming).
> ENGR UNITS key; EU Val Chan 1 soft key, 51.9, mV/EU soft key, EU LBL Chan 1 soft key, pound, Enter soft key.
> TRIG DELAY key; Chan 1 Delay soft key, −2, mSec soft key.
> A key: MEAS DISP key; Filtrd Input soft key, Time Rec 1 soft key, Avrg soft key.
> B key: MEAS DISP key; Power Spec 1 soft key: COORD key; Next soft key, Log X soft key.
> A&B key: SCALE key; Y Auto Scale soft key.
> UNITS key; Trace Title soft key, hammer ##, Enter soft key.
> START key.

Test Procedure

Once the equipment was set up, a general test procedure was begun by selecting an unvoiced piano hammer and the appropriate corresponding impact plate. The impact plate 36 was screwed into the load cell 34, and the piano hammer 10 was attached to the test apparatus frame 46 using a stud and nut included in the frame.

The hammer 10 was pulled back until the hammershank 12 was against the rubber band 48. While holding the hammer in this position, the reset button on the timing circuit was pushed to reset the timing display to zero and to set the Flip-Flops as discussed below. This was necessary since the timing circuit was single pass, so if the hammershank was pulled back through the beam after the timer was reset, there would be no reading for the actual test.

Once the timing circuit was reset, the START key on the HP 3562A signal analyzer 40 was pushed. This armed the HP 3562A trigger and allowed a reading to occur when the input to channel 1 from the load cell 34 reached a certain voltage (approximately 80 millivolts). The hammer 10 was then pulled back slightly more to stretch the rubber band 48 and to provide the necessary initial velocity to the hammer.

When the hammer was released, the hammershank 12 swung down (arrow H) through the laser beam (B) of the timing circuit, starting and stopping the timing circuit to record a time of passage (FIG. 3A). The hammer then struck the load cell impact plate 36 to trigger the HP 3562A to record the Force versus Time record and the Power Spectrum for the impact. If the timer showed a reading of 2.35 to 2.55 milliseconds (94 to 102 inches per second or 2.39 to 2.59 meters per second), the data in the HP 3562A was accepted by pushing the "yes" key on the HP 3562A. (See below for discussion of selection of this velocity for testing.) The hammer was then pulled back against the rubber band, the timing circuit was reset, and the hammer was released. If the timer reading was not acceptable, the "no" button on the HP 3562A was pushed and the process was repeated until four consistently timed sets of data were accumulated and averaged together by the HP 3562A for the selected hammer. The time trace and the power spectrum were then stored on a 3.5 inch floppy disc, e.g. using "UVHF##" (unvoiced hammer frequency data) or "UVHT##" (unvoiced hammer time data) with the number of the hammer as the file name for easy recognition at a later date.

The process was then repeated using the voiced hammer of the same number, with the same impact plate. Once both piano hammers of a particular number were tested, a new hammer was selected and the procedure was repeated until all 88 pairs of unvoiced and voiced piano hammers had been tested and the results recorded.

Initial work was performed to determine the type of testing and data most useful for determining differences between piano hammers.

Figure 5A:
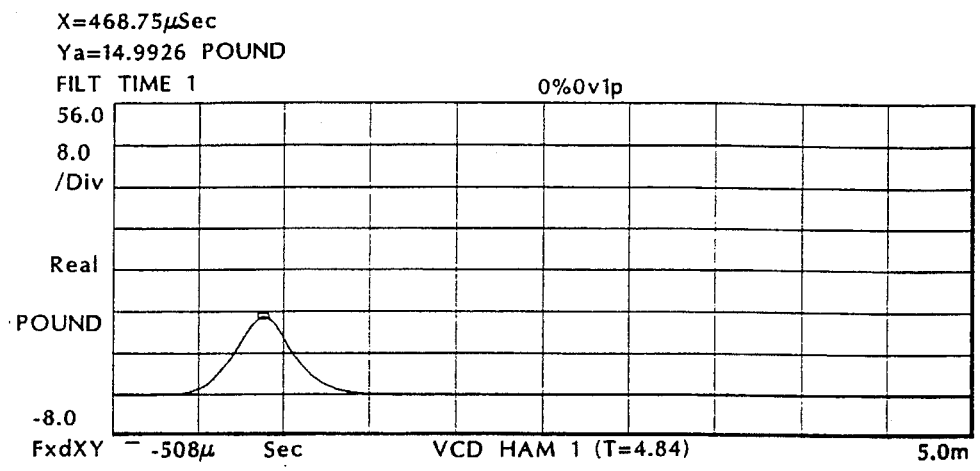
FIGS. 5A, 5B and 5C are plots of Force data for a voiced hammer #1.
Figure 5B:
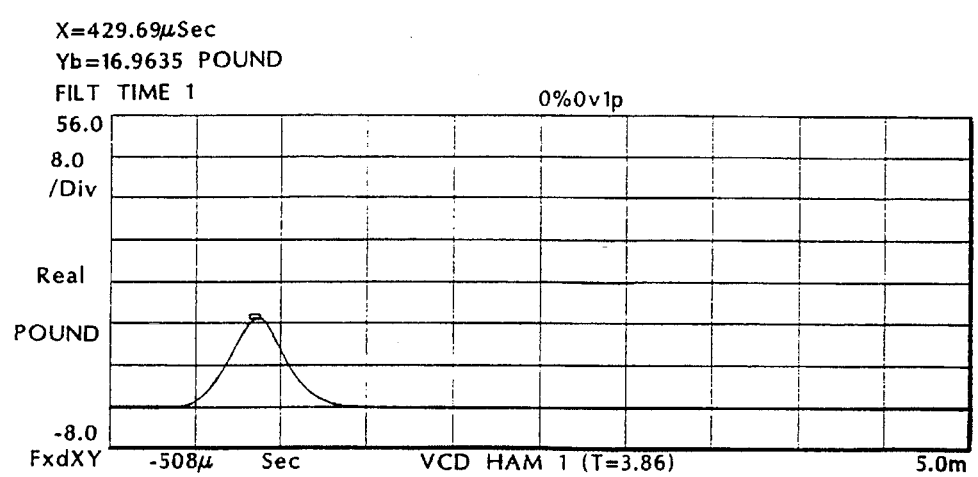
Figure 5C:
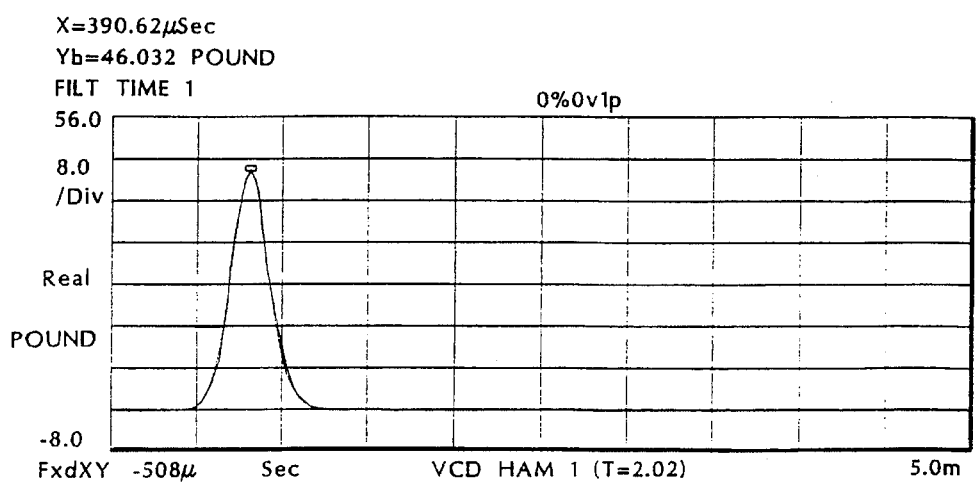
Figure 6A:
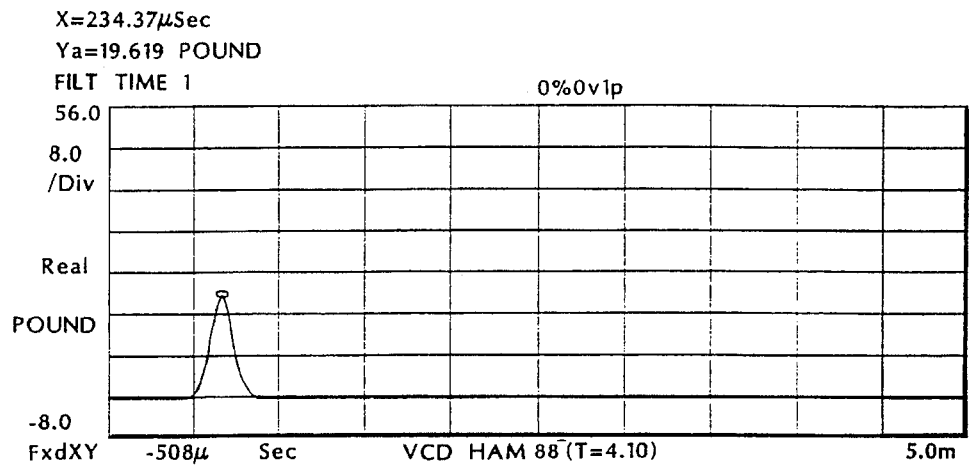
FIGS. 6A, 6B and 6C are plots of Force data for a voiced hammer #88.
Figure 6B:
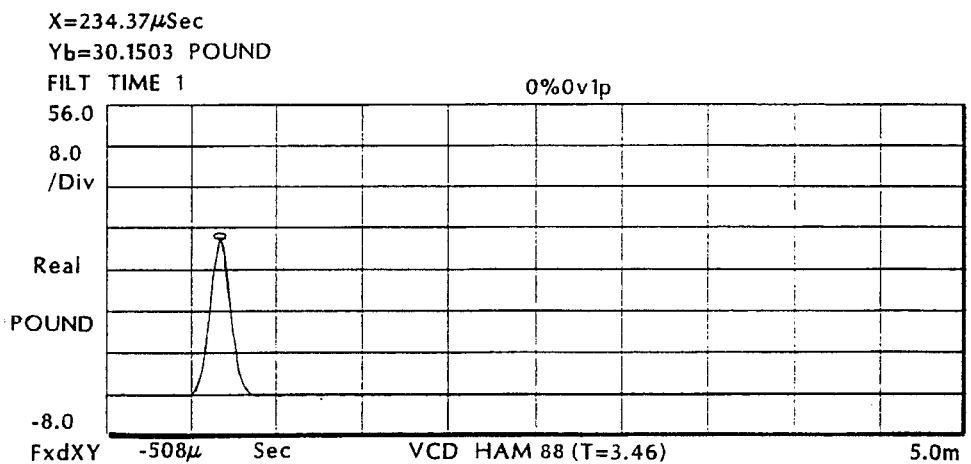
Figure 6C:
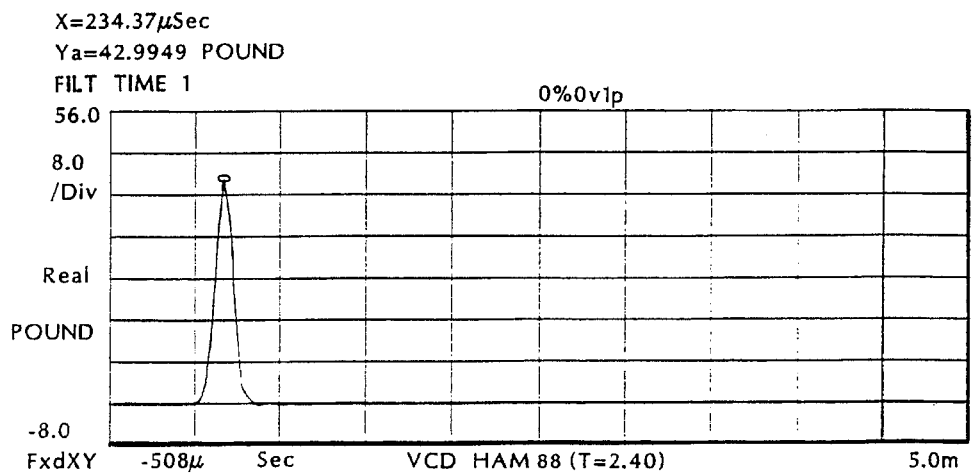

Initially, the Force versus Time data traces for the hammers was evaluated. Samples of this type of data for voiced hammer #1 and voiced hammer #88 at several different velocities can be seen in FIGS. 5 and 6, respectively. Each figure contains three traces for each hammer, with the ordinates and abscissas for each trace being identical to allow for direct comparison of the curves. The (a) trace in each figure is the longest time, thus the slowest speed and the softest impact, for each hammer. Similarly, the (b) trace is the middle speed and the (c) trace is the highest speed strike for each hammer. As may be seen through examination of these traces, no one time domain quantity shown provides sufficient data to quantify the differences between the hammers. For example, FIG. 5(c) shows hammer #1 with a peak force of 46.03 pounds (204.7 newtons) at a velocity of 119 inches per second (3.023 meters per second). FIG. 6(c) shows hammer #88 with a peak force of 42.99 pounds (191.2 newtons) at a velocity of 100 inches per second (2.54 meters per second). If these two hammers were tested at exactly the same speed, the peak force would be extremely close and another factor such as width of the impulse at the one-half peak force point would be a necessary additional quantity to be examined. It may be noted that the pulse duration decreases as the velocity increases, so velocity control would still be necessary, and other complications such as where to measure the pulse width ($\Delta\tau$ at $F_{max}/2$, or some other point) would become apparent. This makes comparison complex and thus not a readily usable solution.

Various different criteria have been proposed for examination of data. For example, Ingolf Bork of West Germany performed work using the Shock Spectrum, as defined below, to perform studies of mallets for use on the xylophone. He performed these studies by hitting the mallet on a load cell and reported that the method might be useful in dealing with piano hammers. However, since proper Shock Spectrum analysis requires variation of damping in the impacting object, and since we were not changing the piano hammer design, only measuring them, Shock Spectrum analysis was not employed as a measure.

Another group investigating piano hammers (Askenfelt and Jansson of Sweden) performed experiments by examining time domain records and Power Spectra of the velocity of the string. (The Power Spectra of the force is a plot of the square of the amplitude of the spectral components of the force versus their oscillation frequency, as described in more detail below in the section headed "Statistical Energy Quantities Used for Vibrational and Acoustical Analysis".) However, in order to accumulate the data they required, they had to include in their testing the interface between the string and the piano hammer and both of these objects had to be instrumented. The method presented here is simpler because the string-hammer interface consideration and more complex instrumentation were proven unnecessary. As far as can be determined, Askenfelt and Jansson never directly measured the impact force through use of a load cell.

Figure 7A:
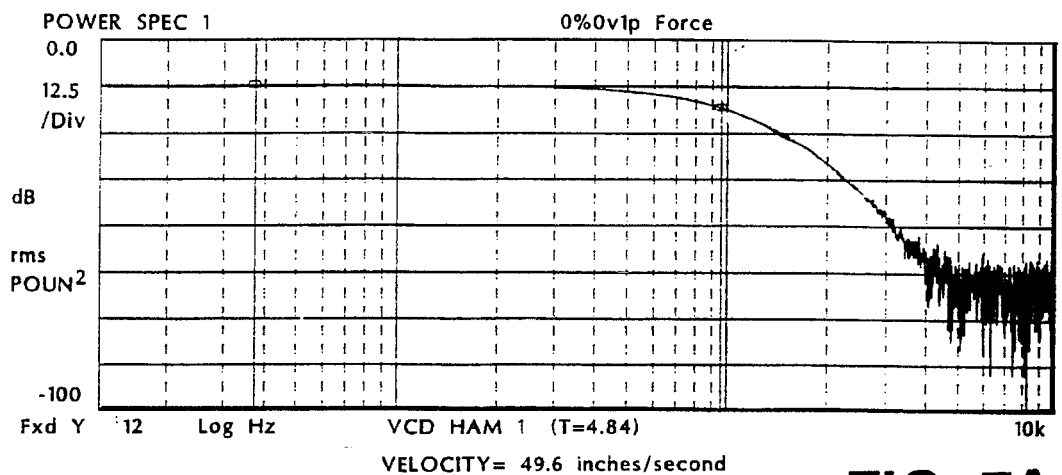
FIGS. 7A, 7B and 7C are plots of Power Spectra data for a voiced hammer #1.
Figure 7B:
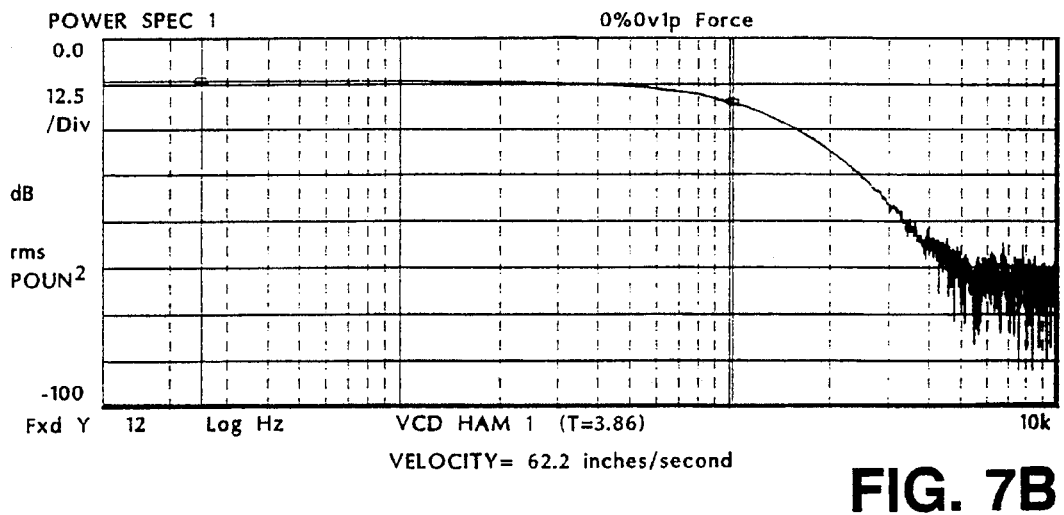
Figure 7C:
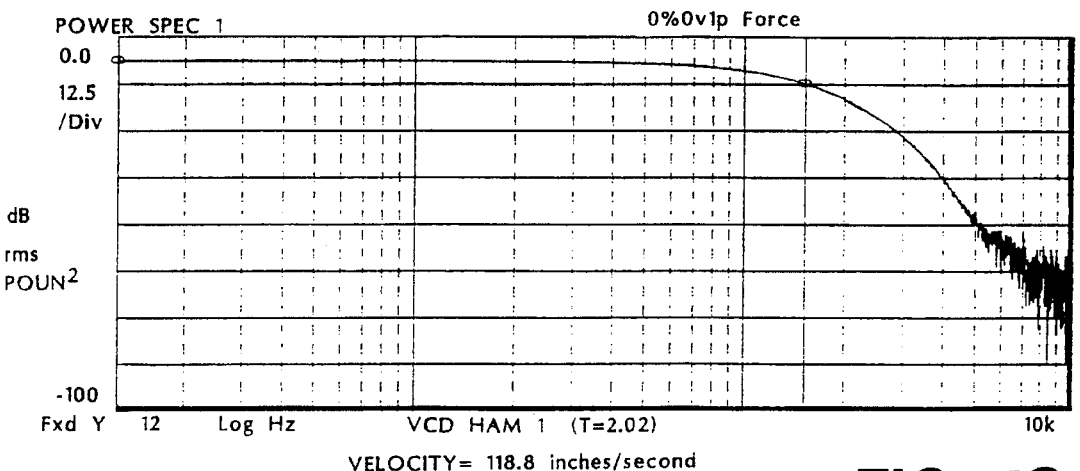
Figure 8A:
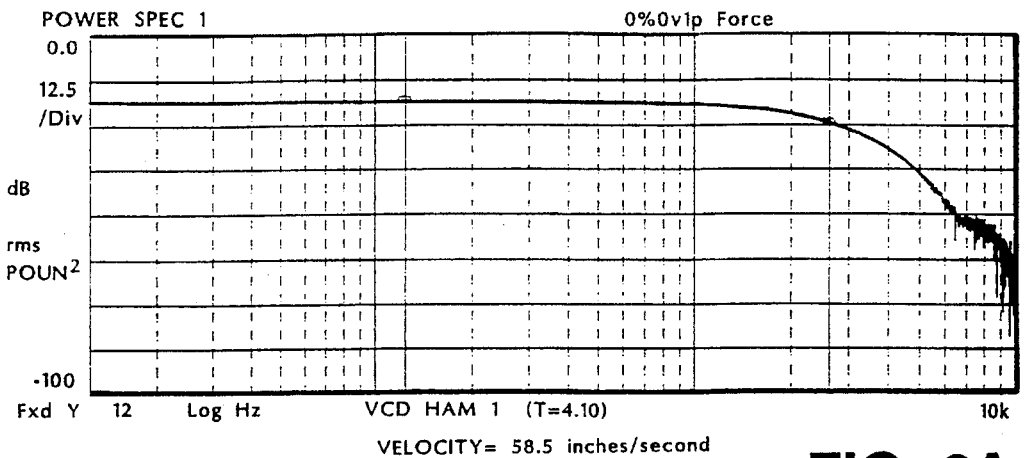
FIGS. 8A, 8B and 8C are plots of Power Spectra data for a voiced hammer #88.
Figure 8B:
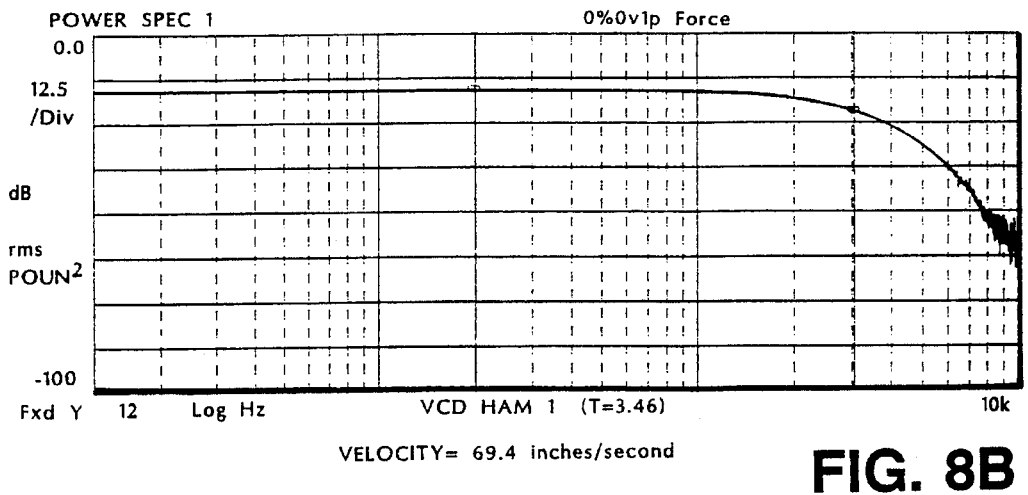

According to the invention, the impact data after transformation into the frequency domain was examined with use of some criteria on the Power Spectra of the Force versus Time traces. The Power Spectra for voiced hammer one and for voiced hammer 88 can be seen in FIGS. 7 and 8, with the velocities being identical to those used in FIGS. 5 and 6, respectively. The traces shown in FIGS. 7 and 8 are shown using a logarithmic scale for the frequency axis (x axis), and a maximum value of 10 kilohertz, to emphasize the frequencies in the lower range. This emphasis was appropriate because the frequency of the highest note on a piano is only 4186 hertz (as is shown in Table 3) and only electronic noise from the instrumentation was visible at the high end of this range. FIGS. 7 and 8 show clear differences between the voiced hammers at each velocity shown. It should be noted that the HP 3562A signal generator uses 800 equally spaced data points in the frequency domain. Therefore, since the frequency span used for testing was 0 to 10,000 hertz, the lowest frequency measured and displayed is 10,000/800, or 12.5 hertz. The graph abscissa labelled "value" shown in the figures is truncated to 12 hertz, although the curves shown actually correspond to the initial value of 12.5 hertz.

Figure 8C:
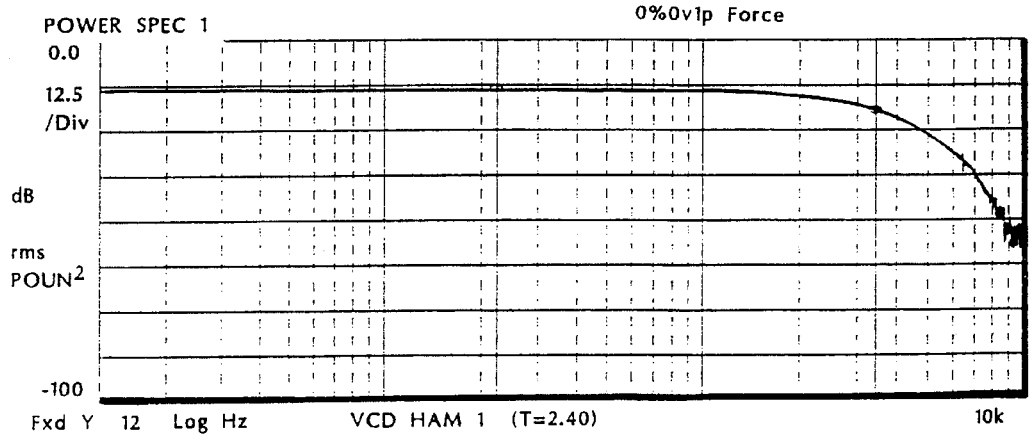

One method of quantifying the differences in the Power Spectra discussed above is to determine the frequency at which the Power Spectrum curve fell to six decibels below its peak value. This frequency, will be referred to as the cut-off frequency, represents the point at which the hammer excites frequencies at one-half of the force spectral amplitude corresponding to the frequency at the peak force amplitude spectral component. The Power Spectra of the force is a plot of the square of the amplitude of the spectral components of the force versus their oscillation frequency. The peak value, which is shown by the left marker in the figures, of the Power Spectrum was determined using the "MRKR PEAK" soft key accessed through the "SPCL MARKER" hard key from the "MARKER" key group. After the peak value of the Power Spectrum was found, the cut-off frequency was determined as discussed above and it is shown for each trace in FIGS. 7 and 8 as the "X" value in the upper left hand corner of each trace. Now, using the sample traces for the two hammers and velocities used above, we look at FIGS. 7(c) and 8(c). As may be recalled, comparison of FIGS. 5(c) and 6(c) did not show any single definitive difference. However, comparison of the cut-off frequencies for FIGS. 7(c) and 8(c) show that the cut-off frequency for voiced hammer #1 is 1.53 kilohertz and the cut-off frequency for voiced hammer #88 is 3.46 kilohertz which is a distinct difference. It may also be noted that the cut-off frequency is more stable with respect to velocity variations than is the peak force or width at the half peak point on the Force versus Time curve. Therefore, this criteria can be used as a single definitive measure for the differentiation of piano hammers, or for the state of tonal regulation of the individual hammers. This method of determination also is particularly applicable since it provides useful information about the frequencies that the given hammer will excite in the struck string at a given velocity as well as the relative levels of that excitation.

Figure 9:
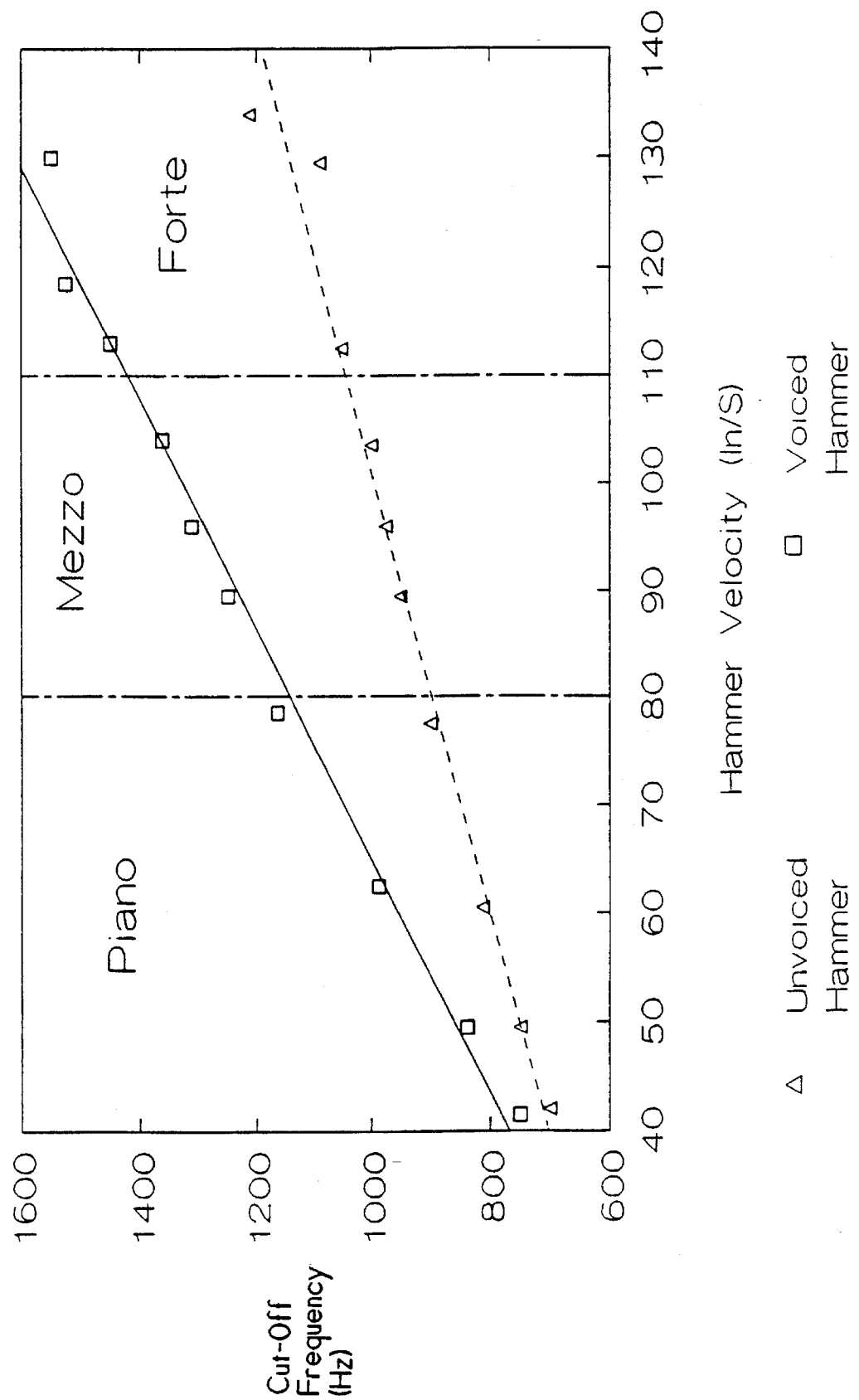
FIGS. 9 is a plot of cut-off frequency versus hammer velocity for a hammer #1.

Examination of FIG. 9 reveals that although the cut-off frequency is relatively stable (as discussed above), there is a definite slope when the cut-off frequency is plotted against the hammer velocity. The slopes for the two curves shown in FIG. 9 (for hammer #1) are 4.876 hertz per inch per second for the unvoiced piano hammer and 9.350 hertz per inch per second for the voiced piano hammer. Therefore, in order to maintain consistency in the results, the velocity should be controlled. Also, it was felt that the results of testing would be most representative if the velocity used were equivalent to that of a pianist playing at the mezzo piano or mezzo forte level. In order to determine the appropriate velocity, the action was removed from the Steinway & Sons, Model M grand piano and placed on a table. The timing apparatus described was set up with the laser on one end of the action and the photo transistor on the other end of the action and adjusted so the beam struck the same position on each hammershank. Also, a board was positioned above the hammers at approximately the same distance as the strings to provide restraint so the hammershanks would not break at the end of their travel.

Using this set-up, a pianist was invited to "play" the keyboard at various volume levels and the hammer velocities were recorded. The approximate ranges are indicated in FIG. 9. A testing velocity of 94 to 102 inches per second (2.38 to 2.59 meters per second) was chosen as the approximate middle of the mezzo range of velocities and as a sufficiently small range to provide comparable data.

Figure 10A:
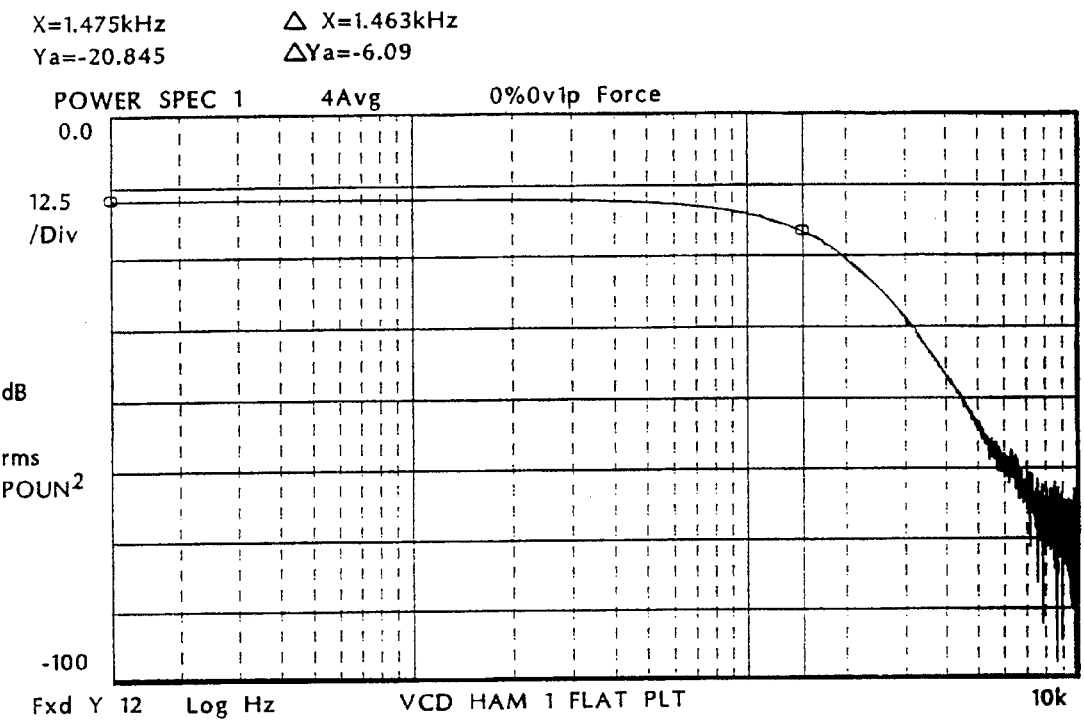
FIGS. 10A and 10B are plots of Power Spectra data for a hammer pair #1 hitting a flat plate.
Figure 10B:
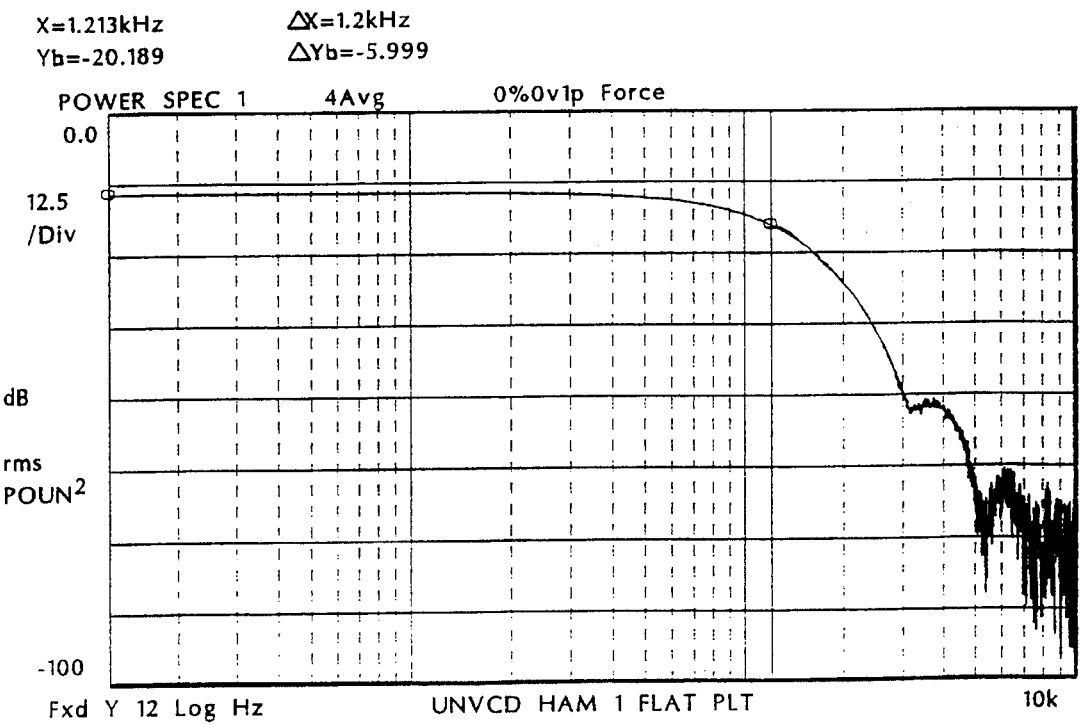
Figure 11A:
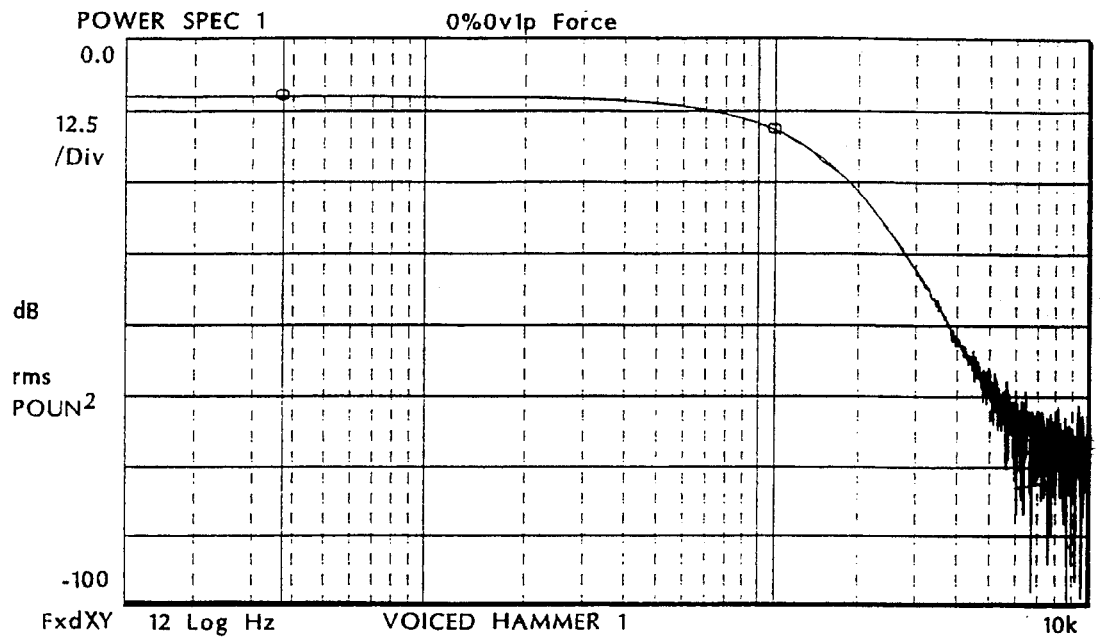
FIGS. 11A and 11B are plots of Power Spectra data for a hammer pair #1 hitting a string replica.
Figure 11B:
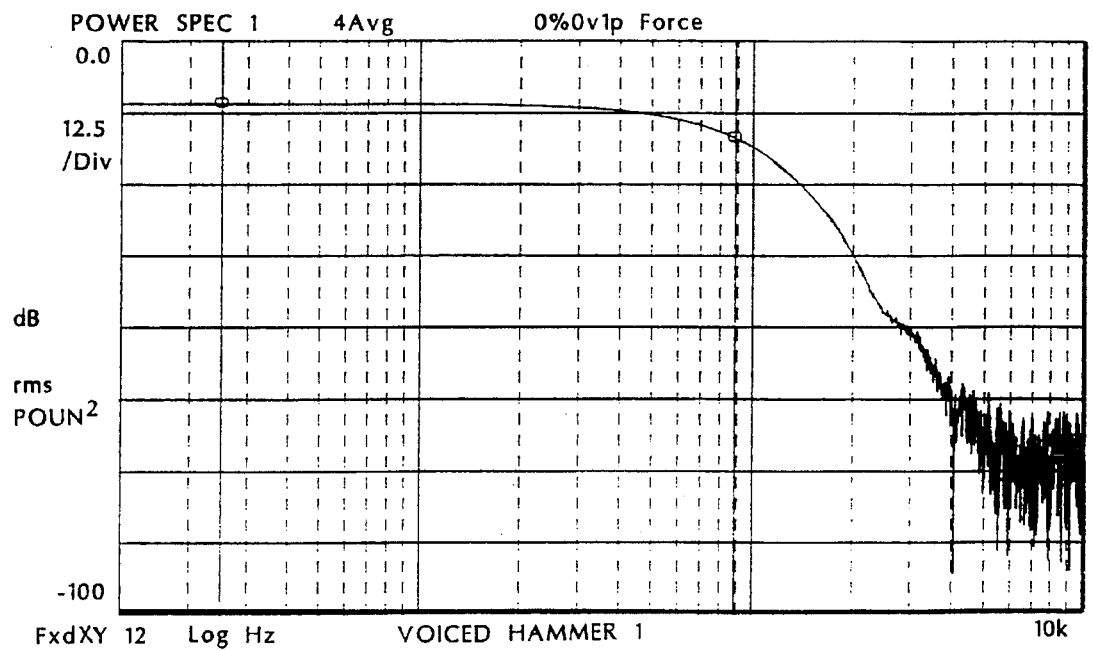
Figure 12A:
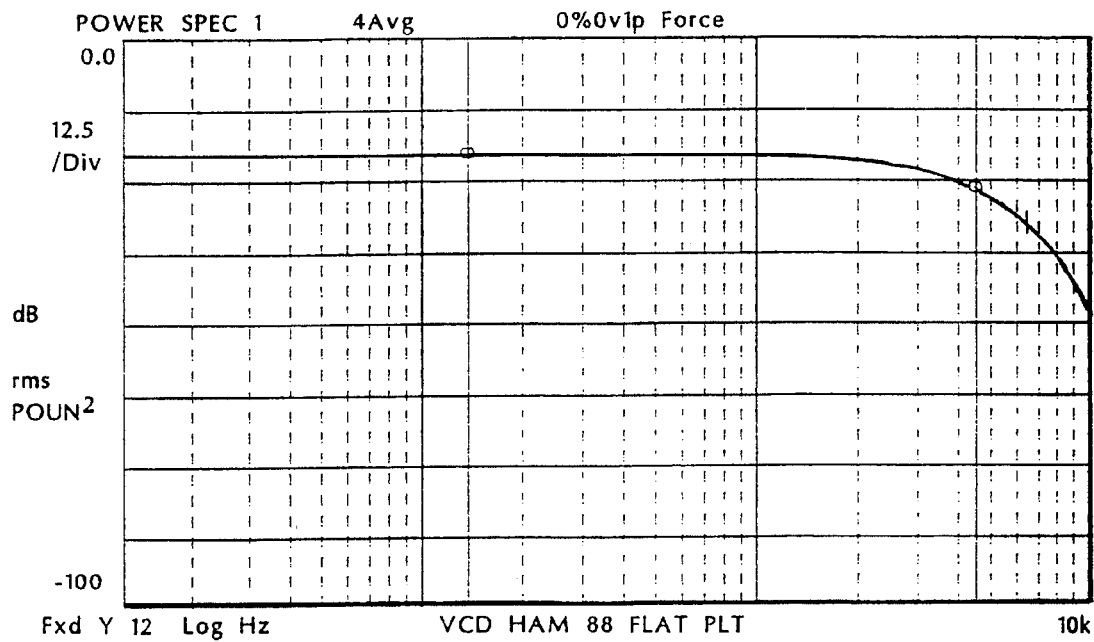
FIGS. 12A and 12B are plots of Power Spectra data for a hammer pair #88 hitting a flat plate.
Figure 12B:
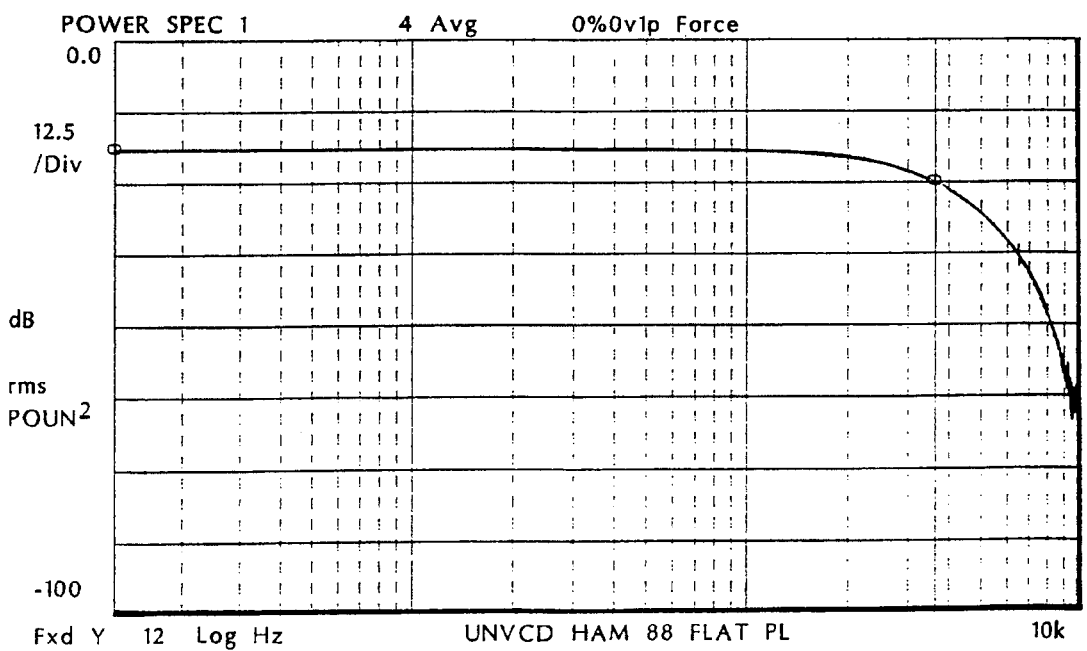
Figure 13A:
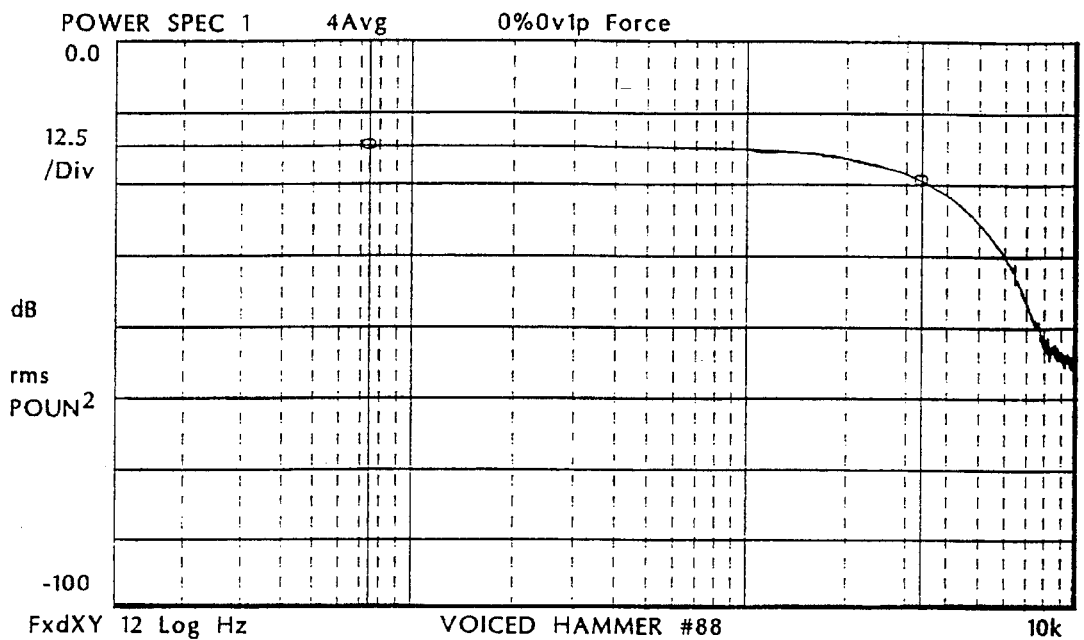
FIGS. 13A and 13B are plots of Power Spectra data for a hammer pair #88 hitting a string replica.
Figure 13B:
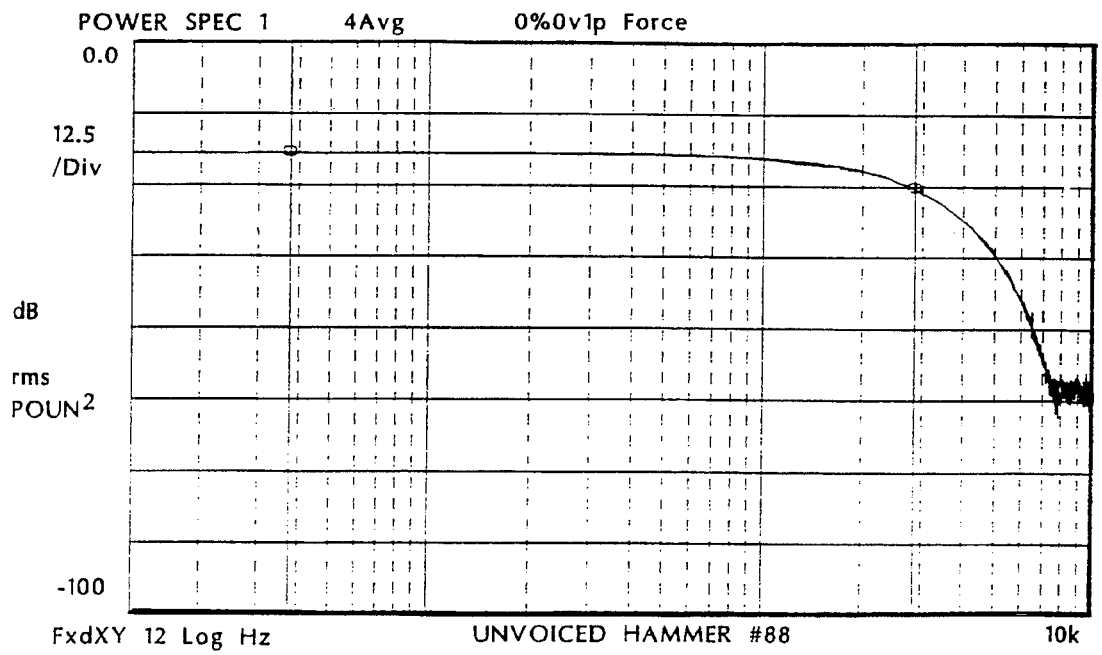

In order to make the results as directly applicable to the piano as possible, it was decided that the piano hammers should strike a surface closely resembling the string configuration against which it is normally struck. The differences between the curves produced by hammer strikes against flat plates versus plates shaped like piano strings is quite dramatic. This is best illustrated by comparing the cut-off frequencies for hammer pairs #1 and #88. FIG. 10 shows the Power Spectra for hammer pair #1 when struck against a flat plate and FIG. 11 shows the same information when the hammers are struck against a shaped impact plate. As may be seen, the piano hammers have a cut-off frequency which is 300 to 400 hertz higher when struck against a flat plate (FIG. 10) instead of string replica impact plate (FIG. 11). This result is even more dramatic (an increase of 800 to 1200 hertz) for hammer pair #88 striking a flat plate, as seen in FIG. 12, instead of the string replica plate, as seen in FIG. 13. Considering these results, it was decided that the most useful data for work with piano hammers could be attained only if the shape of the strings were simulated, as will be described more fully below.

Figure 14A:
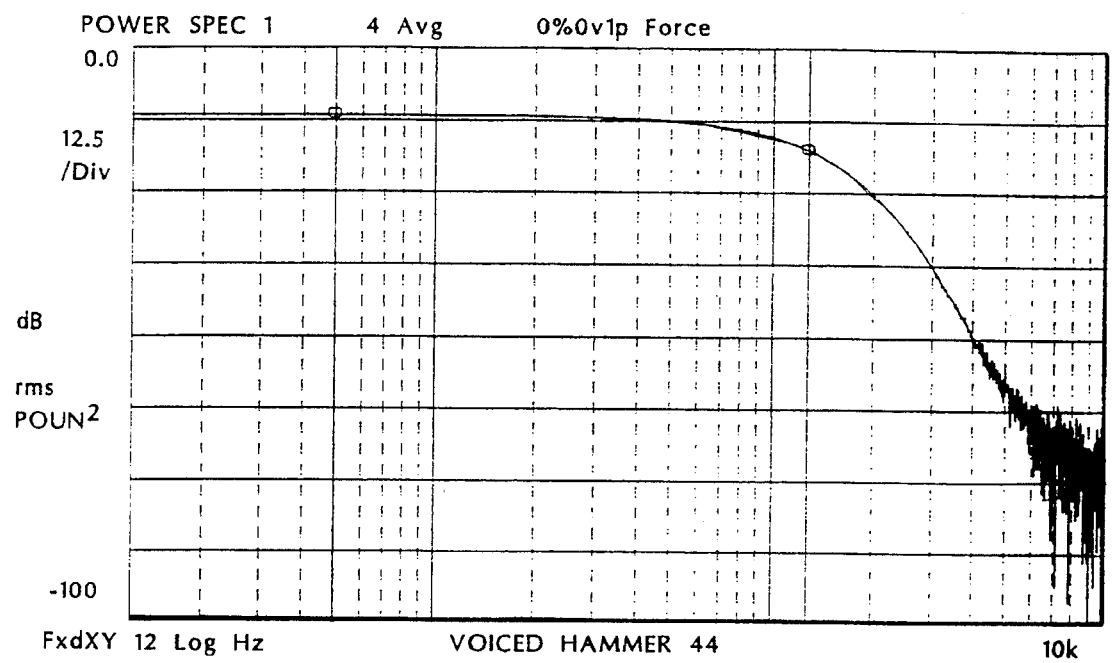
FIGS. 14A and 14B are plots of Power Spectra data for a hammer pair #44.
Figure 14B:
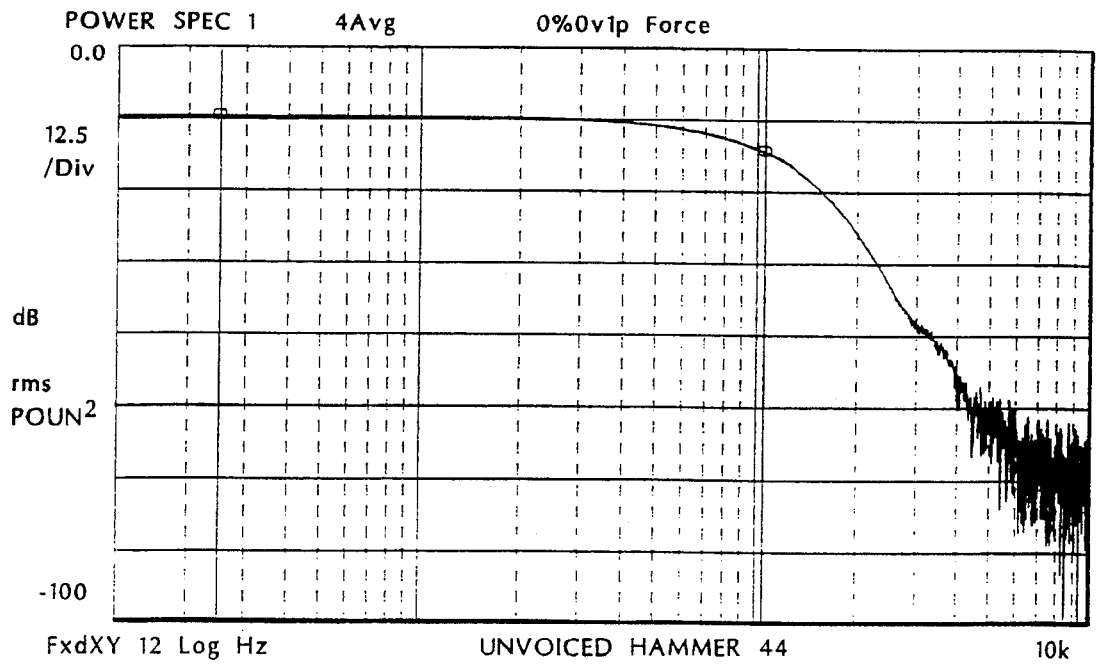
Figure 15A:
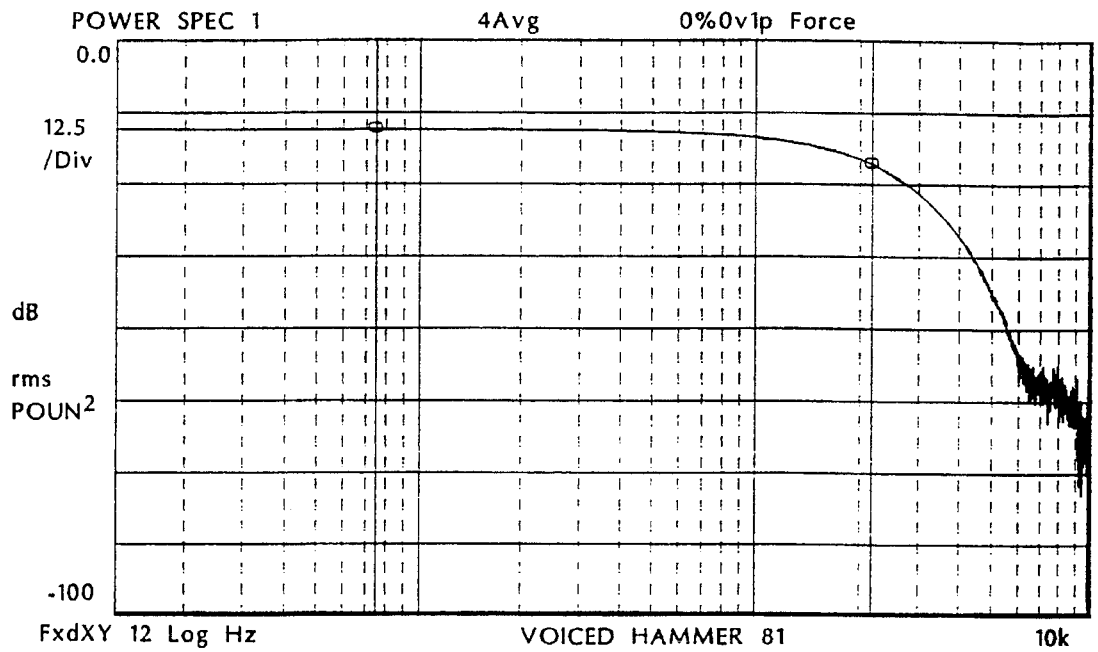
FIGS. 15A and 15B are plots of Power Spectra data for a hammer pair #81.
Figure 15B:
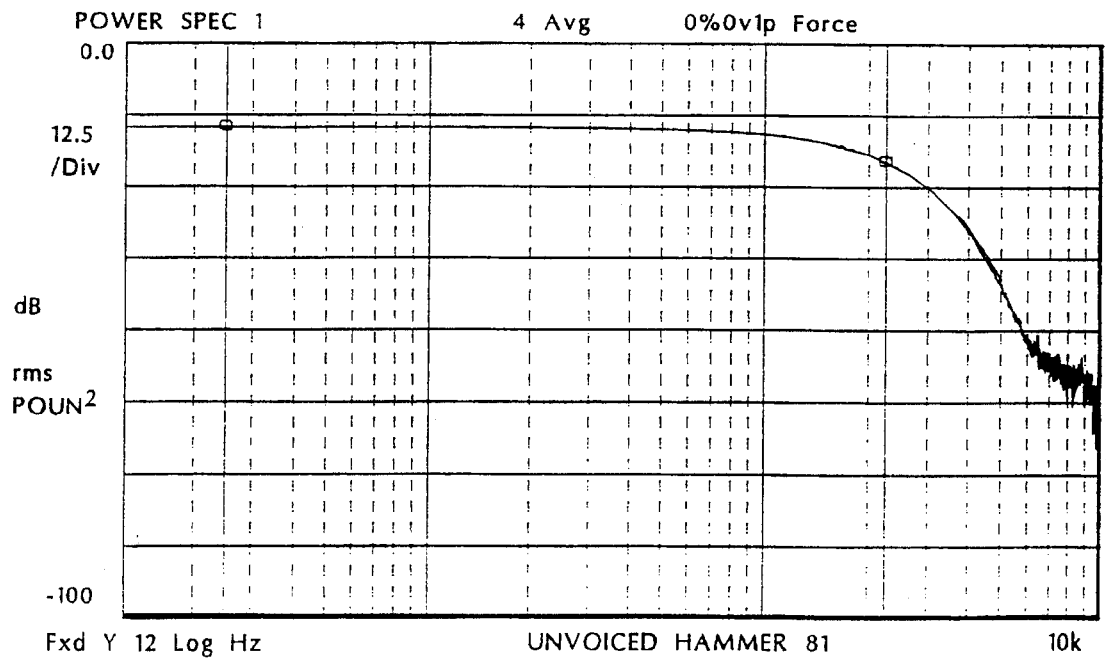

The ability to determine different piano hammers based upon the difference in the cut-off frequency of the Power Spectrum, as discussed above, can also be used to determine the difference between a piano hammer that has been properly voiced and a hammer which needs to be voiced. The Power Spectrum for voiced piano hammer #1 in the trace in FIG. 11(a) and for unvoiced piano hammer #1 in the trace in FIG. 11(b). Data for these two traces, and for all 88 piano hammer pairs, are the average of data taken for four impacts of each hammer, against the appropriate string replica impact plate, with the velocity of each run held between 94 and 102 inches per second (2.38 to 2.59 meters per second). Examination of the two traces shows a difference of 250 hertz in the cut-off frequency of the two hammers with the voiced piano hammer having the higher cut-off frequency. This excitement of higher frequencies by the voiced piano hammer means that it is harder than the unvoiced piano hammer. FIG. 14 shows another example of this relationship which was exhibited by nearly every voiced/unvoiced hammer pair tested. (The only exception was pair #81 in which the unvoiced hammer was harder than the voiced hammer (FIGS. 15 and 19).)

Figure 16:
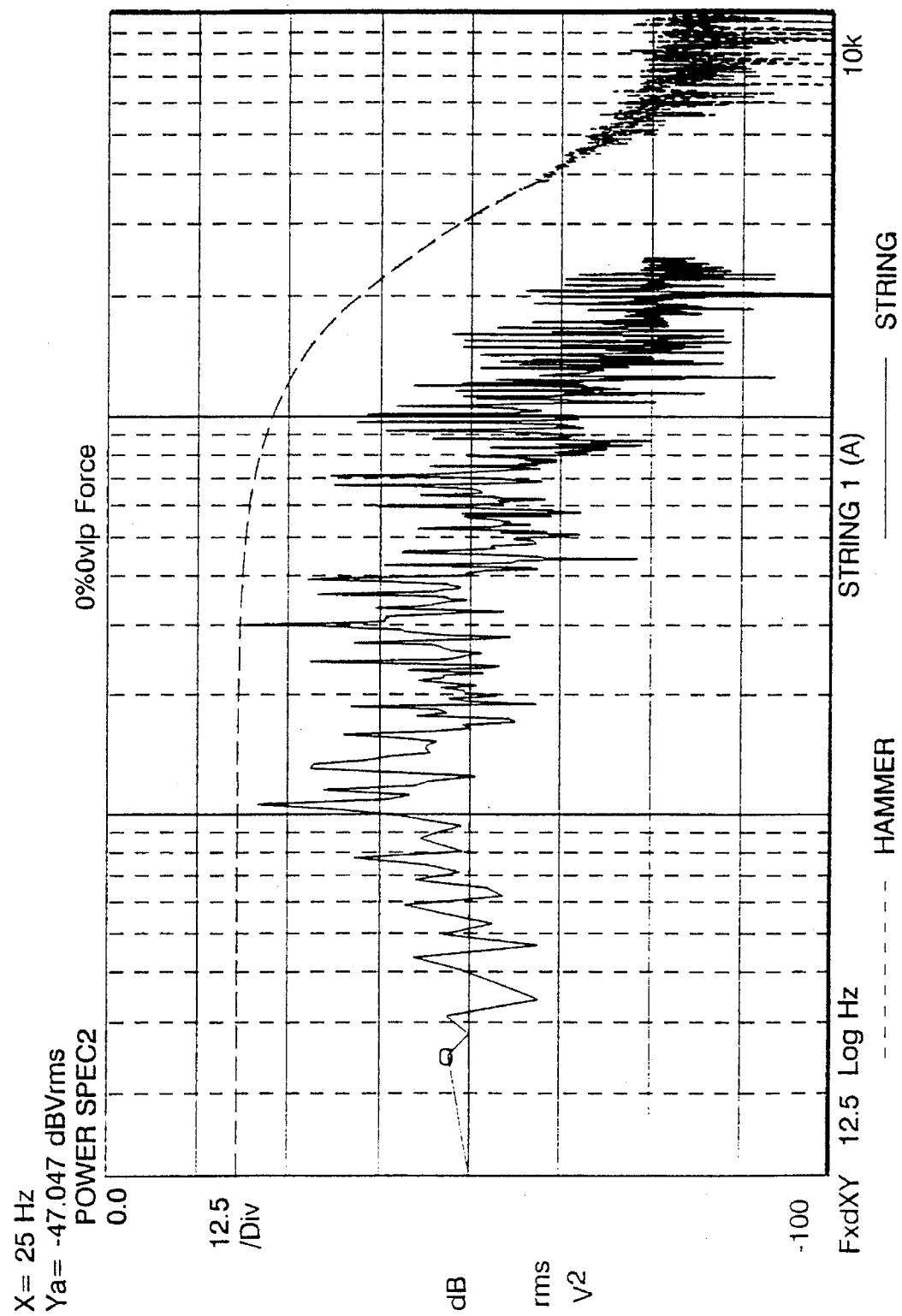
FIG. 16 is a plot of Power Spectra for a voiced hammer #1 load cell output versus a string #1 airborne response at 1.6 feet.
Figure 17:
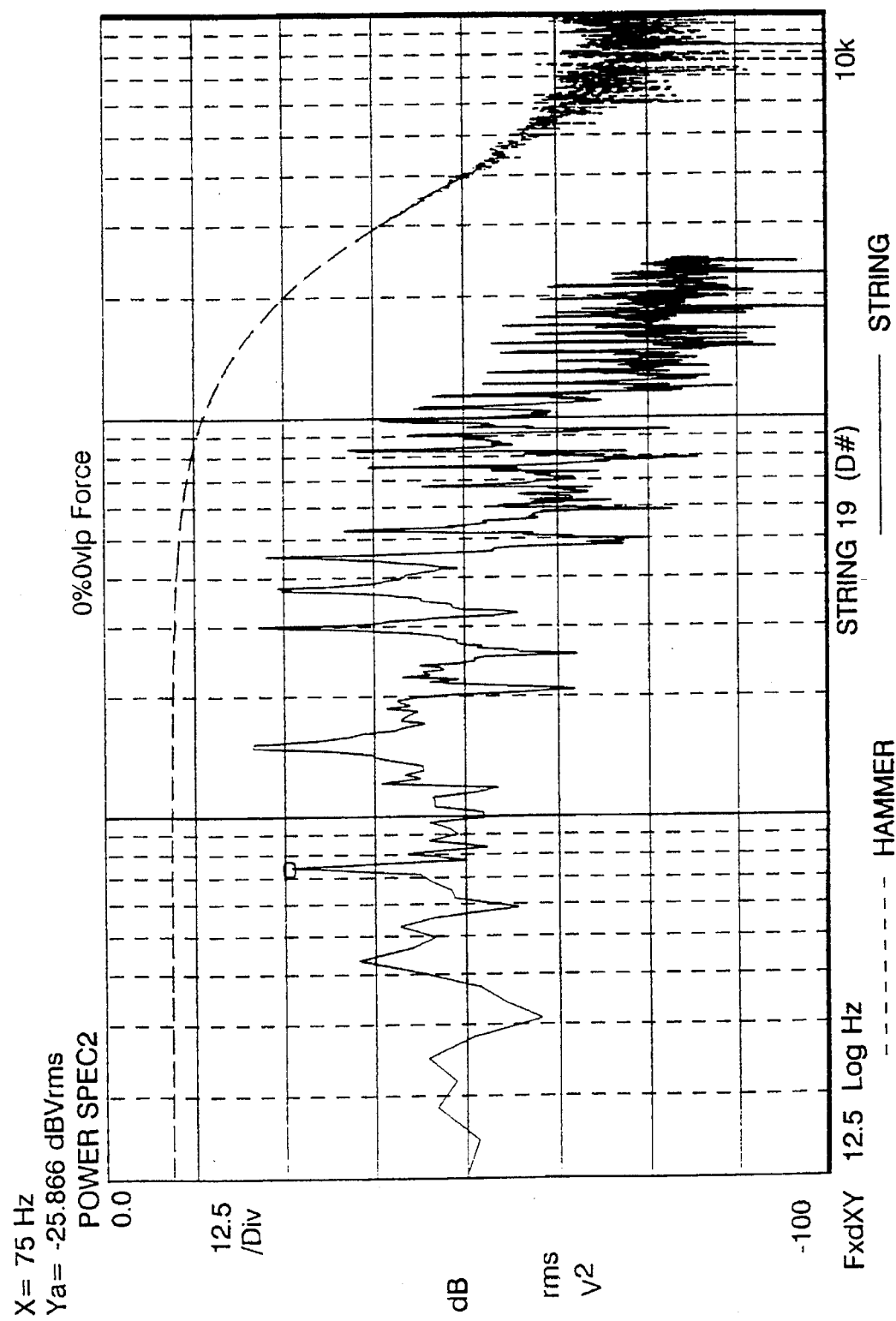
FIG. 17 is a plot of Power Spectra for a voiced hammer #19 load cell output versus a string #19 airborne response at 1.6 feet.
Figure 18:
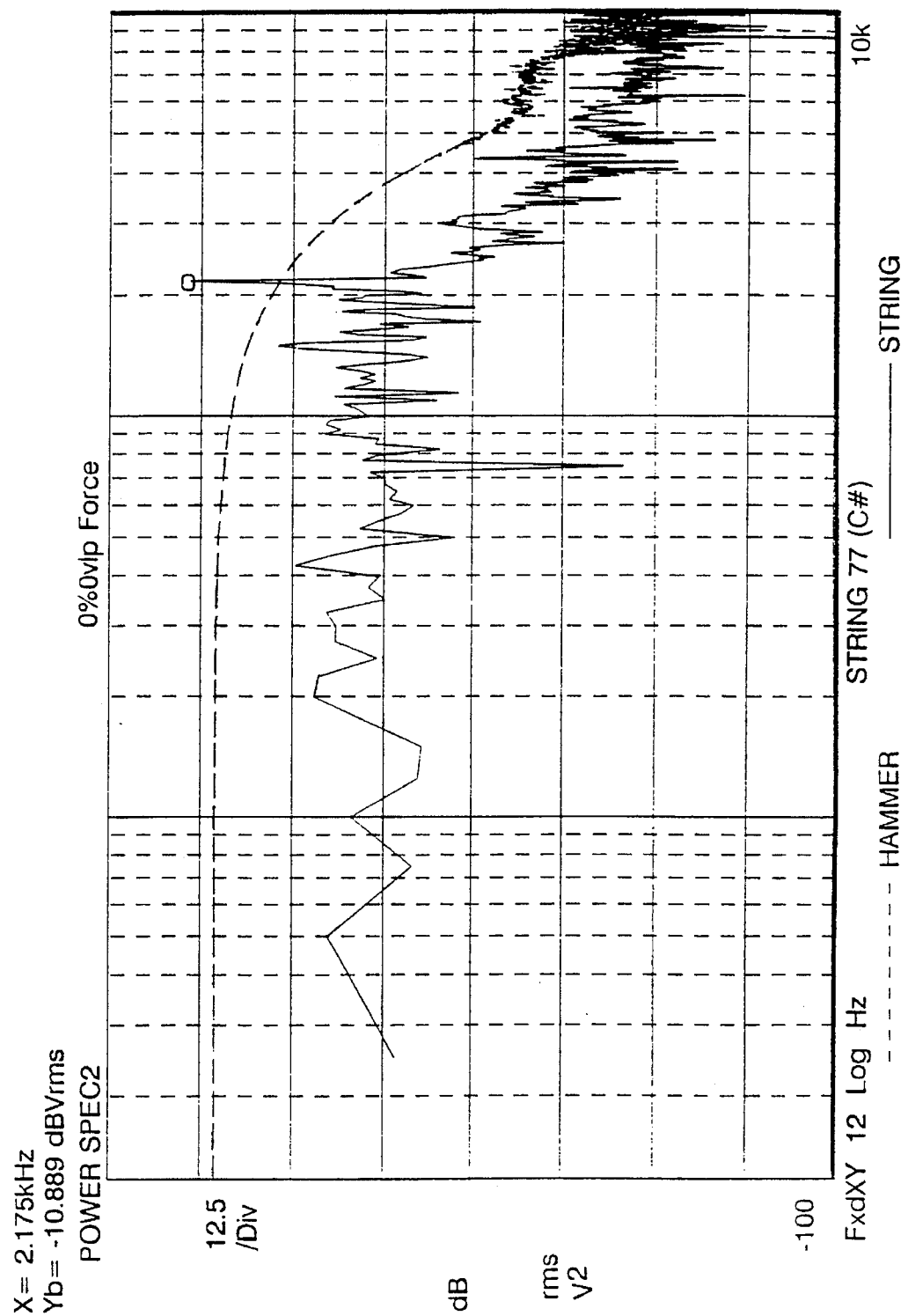
FIG. 18 is a plot of Power Spectra for a voiced hammer #77 load cell output versus a string #77 airborne response at 1.6 feet.

In order to demonstrate the validity of the test method and data, measurements of the Power Spectrum of the sound pressure level of several random piano strings were taken. This was done by placing the Brüel & Kjaer Sound Level Meter (SLM) approximately 1.6 feet (0.5 meters) above the middle of the string being tested. The SLM was set on the C weighting scale because it was the most linear option available on the SLM. The appropriate piano key was then struck and the data recorded on the HP 3562A signal analyzer and converted to a Power Spectrum. These curves were then overlaid onto the Power Spectrum curves of the hammers for comparison. Several of these plots are shown in FIGS. 16–18. It should be noted that since different types of sensors (a load cell versus a microphone) were used for the two measurements, the exact values can not be compared. However, the shape of the curves and the rate at which the power decreases as frequency increases on the hammer Power Spectrum curve predicts quite closely the relative amplitudes of the various partials excited in the struck piano string. Also, in each of these figures, the frequency of the first partial (fundamental frequency) of the string is indicated with a circular marker and the value is displayed in the upper left corner of the figure to within the accuracy of the digital representation of $\Delta f=12.5$ hertz and of course depending on the intonation of the piano. The theoretical values for these strings are: 27.5 hertz for string #1 ($A_O$) shown in FIG. 16; 77.8 hertz for string #19 ($D\#_2$) shown in FIG. 17; and 2217.4 hertz for string #77 ($C\#_7$) shown in FIG. 18.

Examination of FIGS. 16 and 17 reveals that the fundamental frequency of the string is not the most prominent partial. This is due to the restrictions present regarding the length of the bass strings used in a small grand piano. FIG. 18, on the other hand, shows that for piano hammers in the higher registers, the first partial can be dominant.

Figure 19:
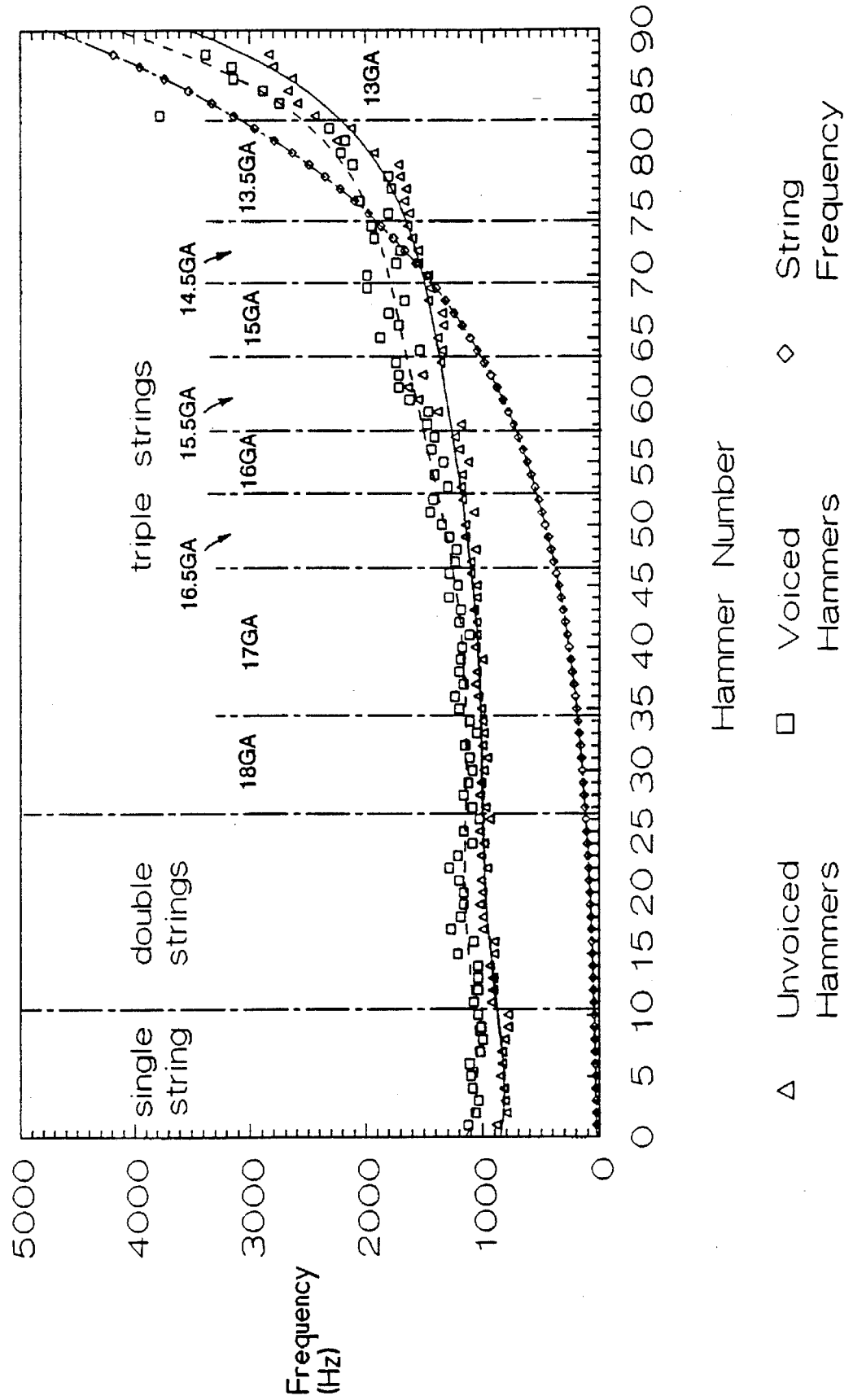
FIG. 19 is a plot of piano hammer cut-off frequencies.

It was thus shown that the method and criteria of the invention are capable of differentiating between piano hammers that are suitable for use for particular notes, and for differentiating between a properly voiced piano hammer and one in need of voicing for a particular note. The values for the cut-off frequencies of all 88 voiced piano hammers and all 88 unvoiced piano hammers, taken at the test velocity of 94 to 102 inches per second (2.38 to 2.59 meters per second), are shown in FIG. 19. FIG. 9 shows that this velocity corresponds to the middle of the mezzo volume range. Also shown in FIG. 19 is the piano string frequency for each note. The values for all of these points are also listed in Table 4. The curves connecting each set of data points are fourth order polynomial regressions of the data.

From the data presented in Table 4, it may be noted that there might be several consecutive hammers in a given piano which are essentially identical acoustically from a cut-off frequency point of view, even after voicing. This is due to the fact that piano hammer voicing is still dependent upon the hearing of a single person and, therefore, on any given day, individual hammers could sound differently to that person. Another example of the dependence upon the individual is shown in the FIG. 19 data point for voiced hammer #83. The cut-off frequency for this hammer is approximately 800 hertz above what would be predicted by the best fit curve through the data. It may also be noted that above voiced hammer #74, the cut-off frequency for the hammers is lower than the fundamental frequency of the string at the tested velocity.

TABLE 4

| Piano Hammer Cut-off Frequencies | | | |
|---|---|---|---|
| Hammer or Key Number | String Frequency | Unvoiced Hammers | Voiced Hammers |
| 1 | 27.500 | 887 | 1125 |
| 2 | 29.135 | 800 | 1063 |
| 3 | 30.868 | 813 | 1037 |
| 4 | 32.703 | 825 | 1087 |
| 5 | 34.648 | 850 | 1100 |
| 6 | 36.708 | 838 | 1112 |
| 7 | 38.891 | 838 | 1025 |
| 8 | 41.203 | 813 | 1000 |
| 9 | 43.654 | 787 | 1013 |
| 10 | 46.249 | 787 | 1038 |
| 11 | 48.999 | 925 | 1075 |
| 12 | 51.913 | 913 | 1038 |
| 13 | 55.000 | 913 | 1038 |
| 14 | 58.270 | 938 | 1038 |
| 15 | 61.735 | 900 | 1213 |
| 16 | 65.406 | 900 | 1075 |
| 17 | 69.296 | 1000 | 1270 |
| 18 | 73.416 | 1000 | 1187.5 |
| 19 | 77.782 | 1025 | 1162.5 |
| 20 | 82.407 | 1000 | 1162.5 |
| 21 | 87.307 | 1012.5 | 1200 |
| 22 | 92.499 | 962.5 | 1287 |
| 23 | 97.999 | 1012.5 | 1213 |
| 24 | 103.83 | 987.5 | 1087.5 |
| 25 | 110.00 | 1025 | 1162.5 |
| 26 | 116.54 | 937.5 | 1025 |
| 27 | 123.47 | 975 | 1087 |
| 28 | 130.81 | 1025 | 1163 |
| 29 | 138.59 | 1013 | 1125 |
| 30 | 146.83 | 987 | 1087 |
| 31 | 155.56 | 963 | 1113 |
| 32 | 164.81 | 1000 | 1150 |
| 33 | 174.61 | 987 | 1050 |
| 34 | 185.00 | 1000 | 1113 |
| 35 | 196.00 | 1013 | 1200 |
| 36 | 207.65 | 1038 | 1238 |
| 37 | 220.00 | 1063 | 1163 |
| 38 | 233.08 | 1050 | 1200 |
| 39 | 246.94 | 1000 | 1187 |
| 40 | 261.63 | 1063 | 1175 |
| 41 | 277.18 | 1050 | 1113 |
| 42 | 293.66 | 1050 | 1200 |
| 43 | 311.13 | 1075 | 1187 |
| 44 | 329.63 | 1050 | 1287 |
| 45 | 349.23 | 1050 | 1213 |
| 46 | 369.99 | 1100 | 1287 |
| 47 | 391.99 | 1100 | 1238 |
| 48 | 415.31 | 1063 | 1225 |
| 49 | 440.00 | 1150 | 1287 |
| 50 | 466.16 | 1150 | 1350 |
| 51 | 493.88 | 1075 | 1450 |
| 52 | 523.25 | 1175 | 1425 |
| 53 | 554.37 | 1187 | 1300 |
| 54 | 587.33 | 1175 | 1413 |
| 55 | 622.25 | 1125 | 1338 |
| 56 | 659.26 | 1200 | 1438 |
| 57 | 698.46 | 1238 | 1413 |
| 58 | 739.99 | 1187 | 1475 |
| 59 | 783.99 | 1387 | 1463 |
| 60 | 830.61 | 1550 | 1625 |
| 61 | 880.00 | 1638 | 1713 |
| 62 | 932.33 | 1513 | 1713 |
| 63 | 987.77 | 1363 | 1738 |
| 64 | 1046.5 | 1350 | 1538 |
| 65 | 1108.7 | 1387 | 1875 |
| 66 | 1174.7 | 1338 | 1713 |
| 67 | 1244.5 | 1350 | 1800 |
| 68 | 1318.5 | 1463 | 1663 |

TABLE 4-continued

Piano Hammer Cut-off Frequencies

| Hammer or Key Number | String Frequency | Unvoiced Hammers | Voiced Hammers |
| --- | --- | --- | --- |
| 69 | 1396.9 | 1450 | 1987 |
| 70 | 1475.0 | 1463 | 1987 |
| 71 | 1568.0 | 1550 | 1737 |
| 72 | 1661.2 | 1550 | 1700 |
| 73 | 1760.0 | 1600 | 1925 |
| 74 | 1864.7 | 1638 | 1950 |
| 75 | 1975.5 | 1625 | 1800 |
| 76 | 2093.0 | 1662 | 2050 |
| 77 | 2217.4 | 1650 | 1775 |
| 78 | 2349.3 | 1700 | 1800 |
| 79 | 2489.0 | 1713 | 2113 |
| 80 | 2637.0 | 1925 | 2213 |
| 81 | 2793.8 | 2250 | 2175 |
| 82 | 2959.9 | 2125 | 2312 |
| 83 | 3136.0 | 2438 | 3775 |
| 84 | 3322.4 | 2587 | 2750 |
| 85 | 3520.0 | 2675 | 2887 |
| 86 | 3729.3 | 2638 | 3137 |
| 87 | 3951.1 | 2800 | 3150 |
| 88 | 4186.0 | 2838 | 3375 |

Figure 20:
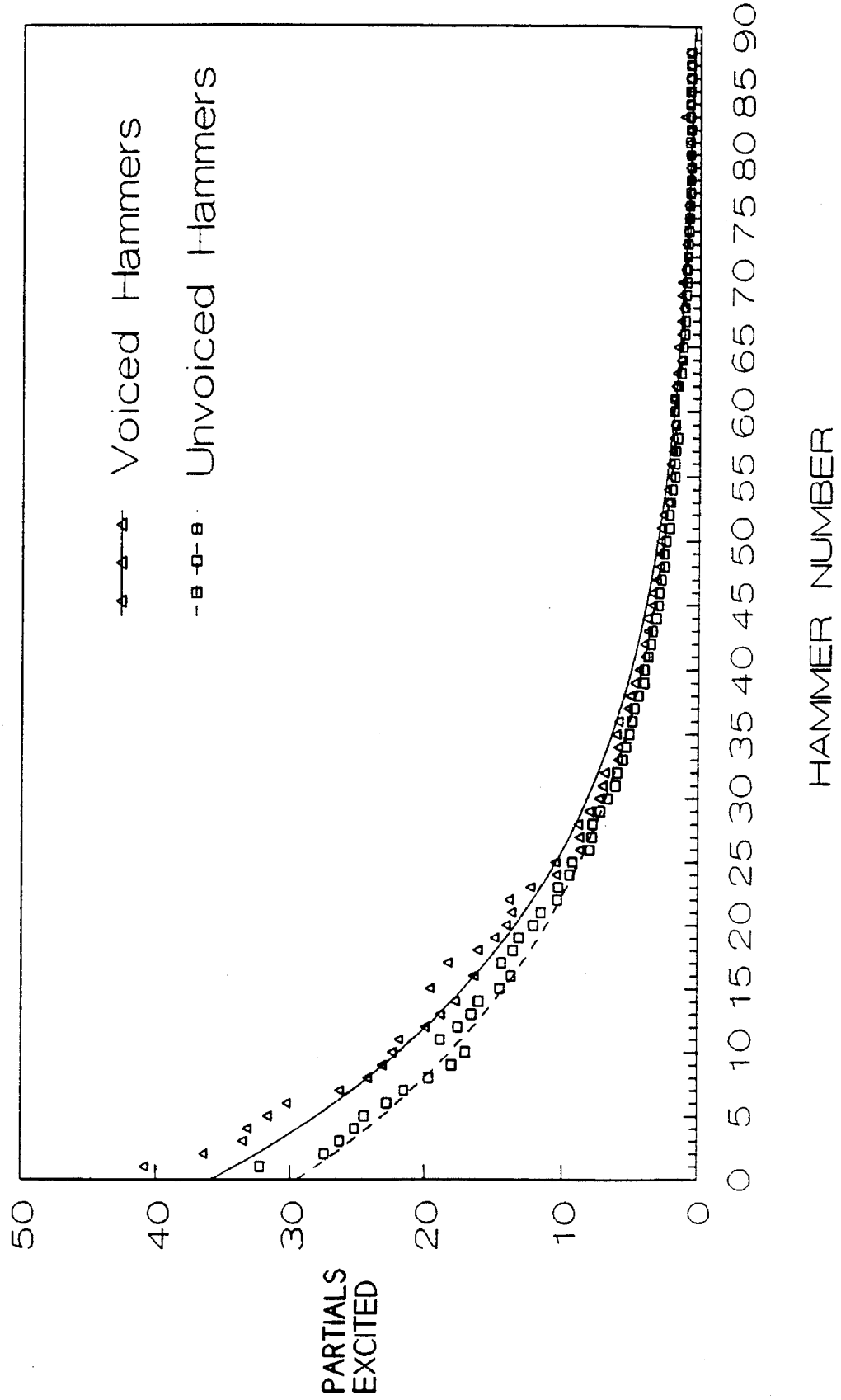
FIG. 20 is a plot of partials excited by piano hammers.

Referring now to FIG. 20, the number of partials excited by a hammer, as calculated by dividing the cut-off frequency (Table 4), by the fundamental frequency of the note in question, is plotted against the piano hammer number. Examination of the curves in this figure shows that the hammers tend to excite many overtones in the bass register and the number of overtones excited tapers off until in the treble register only the fundamental frequency of the string is excited above the one half power point. This data is an exponential decay of partials excited versus the hammer number with the equation of the exponential curve fit for the voiced piano hammers shown below:

$$Y = 35.87 \, e^{-0.048996 \, x}$$

where x is the hammer number and y is the number of partials calculated. This curve was determined by taking the natural logarithm of the cut-off frequencies and performing a linear regression on this data. The standard deviation for this data was 1.2081 and the R value for the data fitting the curve is 0.992796. The slope of the linearized data is the coefficient of x in the exponent and the intercept of the linearized data is the natural logarithm of the coefficient of e. This can be seen by taking the natural logarithm of the exponential equation above with the result being as shown below:

$$ln(y) = ln(35.87) - 0.048996 \, x$$

It is the exponential curve resulting from this regression which best quantifies the sound of a Steinway & Sons small grand piano as voiced by the factory when played at a mezzo level.

The invention thus provides a quantitative method for accurate repeatable determination of the state of tonal regulation of piano hammer felt. The process entails striking a piano hammer against a rigidly mounted load cell to which a replica of the appropriate string has been attached. The method does not require that the compliance of the piano string be taken into account. It also provides more valuable information regarding the power to which frequencies in the string are excited by the hammer.

Timing Apparatus and Circuit

Due to the extremely low mass of the piano hammers, attachment of a low mass accelerometer, or any other contact method of velocity determination, was ruled out due to the effect this would have on the impact. Therefore, it was decided to employ a non-contact timer. Since the diameters of the hammershanks 12 are consistent from one hammer to the next, it was determined that interruption of a single light beam would provide an average velocity over a sufficiently short period of time. Also, since the timing device was to be set close to the point of impact, and the hammers rebounded quite extensively, it was necessary to ensure that the device was single pass, that is, that time was not accumulated over successive passes of the hammershank through the light beam.

Evaluation of the above criteria led to several possible solutions. One solution was a Photo-Gate Timer sold by Pasco Scientific Company of San Francisco, California. This device met all of the requirements but had a space between the light source and the sensor of only several inches. This was an acceptable solution only for testing of individual piano hammers.

The solution chosen was to construct a timing circuit (FIG. 3A) to be triggered by a photo transistor 28 placed at one side of the piano action, or hammer 10, to be tested. A light source 26 (e.g. a Uniphase 0.95 milliwatt, Helium-Neon laser) was placed on the other side of the piano action and aimed at the photo transistor. Use of separate light source and detector added flexibility in spacing and allowed for a gap greater than the width of a grand piano action. Since the light source and receiver were separate units, a Light Emitting Diode (LED) was added to the timing circuit to indicate proper aim of the laser. Application of the timing circuit to a full piano keyboard action may be seen in FIG. 3B.

Figure 21:
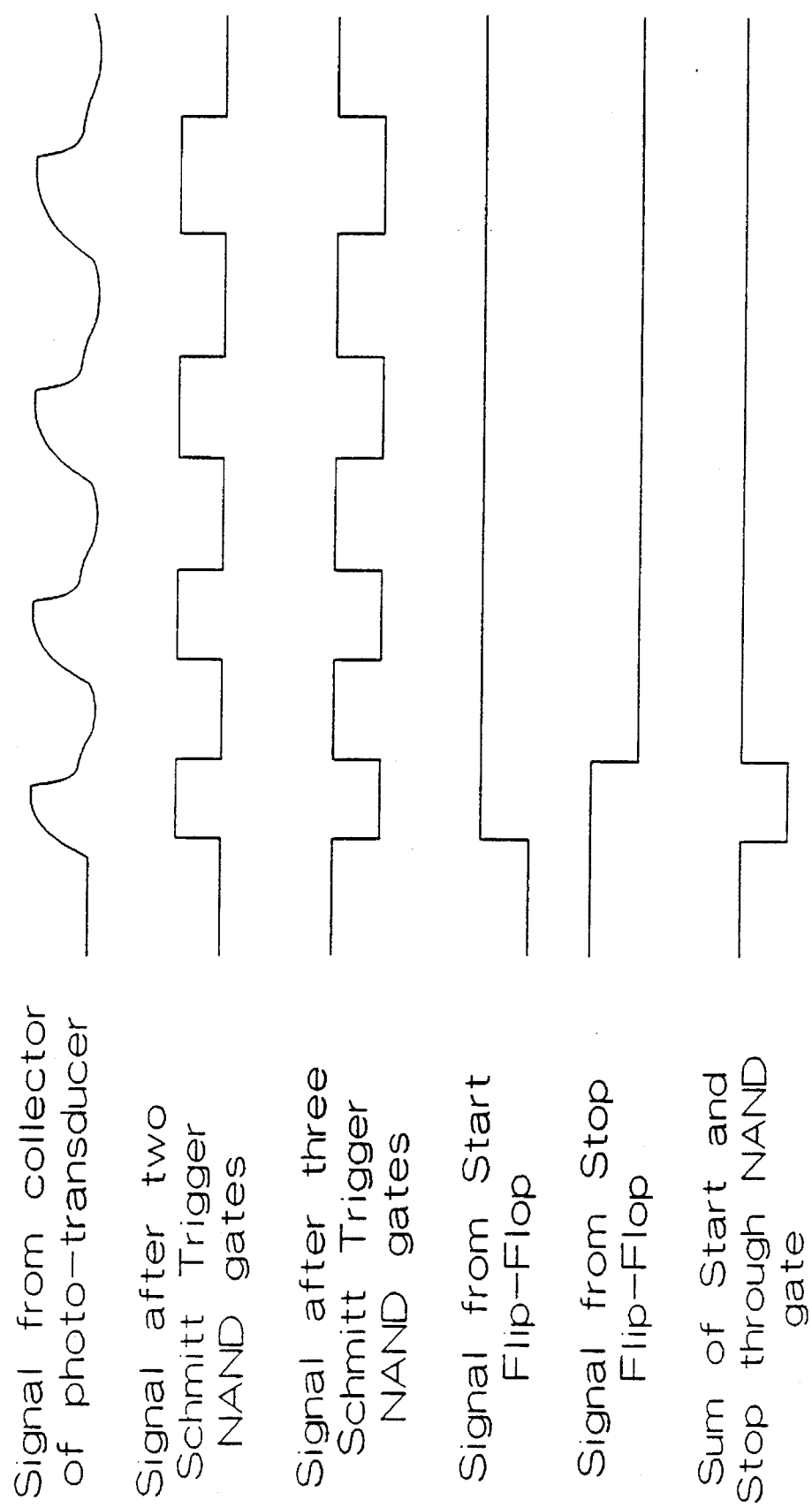
FIG. 21 is an input signal timing diagram.

Referring now to FIG. 21, a trace is shown representing the signal received from the photo-transducer as the hammershank passes through the laser beam, rebounds off the load cell, passes back through the beam, rebounds off the rubber band, passes through the laser beam yet again, and continues in this manner for several cycles.

The shape of the pulses in the top trace of FIG. 21 is due to several factors, including the shape of the piano hammershank, the shape of the laser beam and the speed of motion of the hammershank through the beam. This pulse shape might result in problems in a digital logic circuit because it is not a perfect square wave. Therefore, the signal was conditioned to a square wave pulse by using several Schmitt-Trigger NAND gates as inverters. (A Schmitt-Trigger is a device having a trigger mechanism with hysteresis, i.e., output signal changes from low (0 volts) to high (5 volts) when the input signal crosses a threshold voltage (e.g. 3.5 volts) and from high to low when the input crosses a lower threshold voltage (e.g. 1.5 volts). (The Schmitt-Trigger NAND gates were used in other parts of the circuit for purely economic reasons, i.e. since there are four NAND gates on a 74LS132 chip, they could be used when a NAND gate was needed and a Schmitt-Trigger was not, in lieu of including another chip in the circuit.)

The second design concern suggested by the top trace of FIG. 21 (and also in the next two traces) is the repetition of the pulses. As indicated above, the timing apparatus was required to be a single pass device. Therefore, two D type Flip-Flops, located on one 74LS74 chip, were wired to produce the output signals shown in the fourth and fifth traces of FIG. 21. When the signals were combined through a NAND gate, the result was the single high-low-high pulse shown in the bottom trace of the figure.

After a pass of the hammershank, it was necessary to reset the Flip-Flops to allow a new reading. At the same time, it was appropriate to reset all the counters, and the display, to values of zero. This was accomplished using the push button seen in FIG. 22. When the normally open push button was open, a high (5 volt) signal was sent through a 2.2 kiloohm resistor to the clear line on the start Flip-Flop, the preset line on the stop Flip-Flop and to the load line on all of the counter chips. All of these lines are activated by a low (0 volt) signal. When the push button was depressed, and thus the circuit was grounded, the start and stop Flip-Flops were set to the initial levels shown in FIG. 21 and the counter chips loaded a value of zero as is further explained below.

Figure 23:
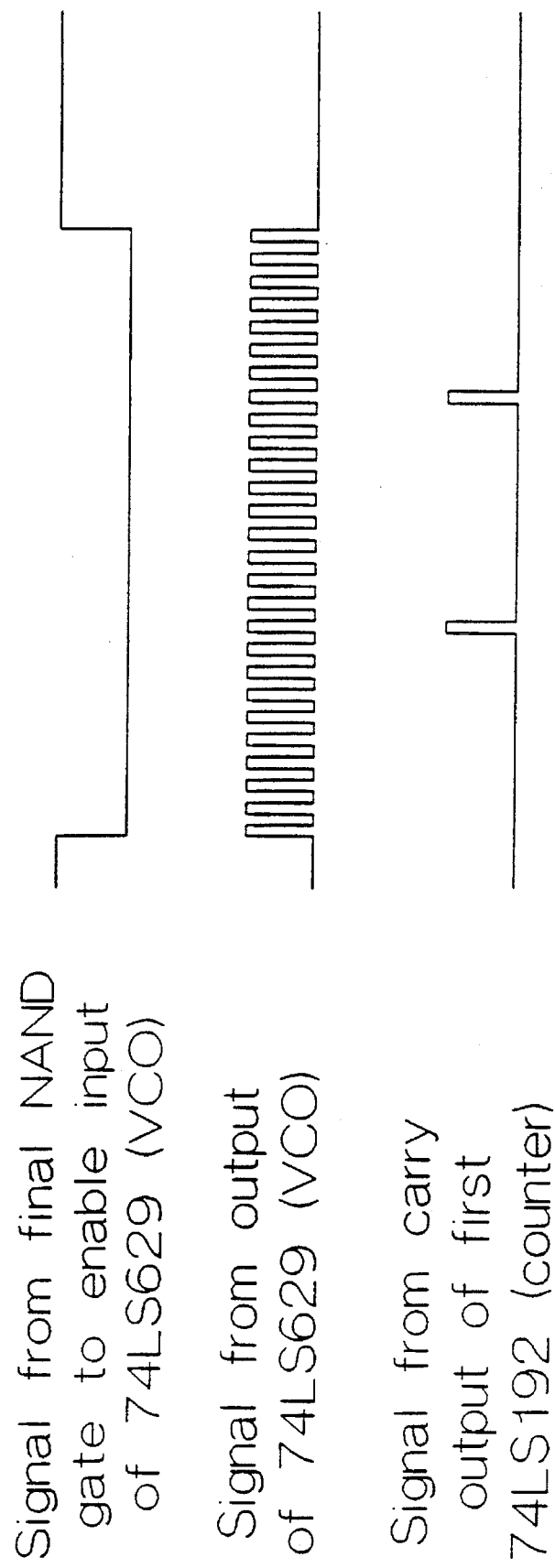
FIG. 23 is a clock signal timing diagram.
Figure 24B:
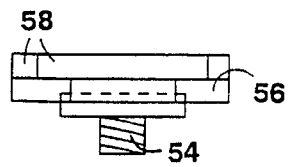
FIGS. 24a–24i are somewhat diagrammatic views of impact plate configurations, FIGS. 24a–24c being plan, top and side views, respectively, of a three string configuration.
Figure 24A:
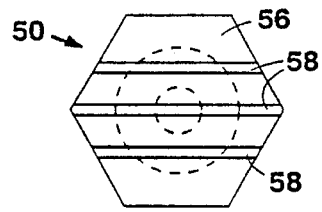
Figure 24C:
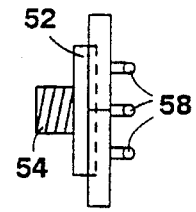
Figure 24E:
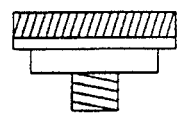
Figure 24D:
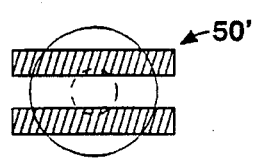
Figure 24F:
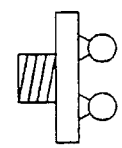
Figure 24H:
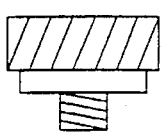
Figure 24G:
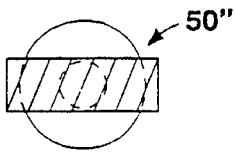
Figure 24I:
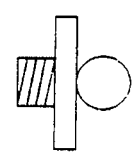

The pulse shown in the bottom trace of FIG. 21 was fed into the Enable line of the Voltage Controlled Oscillator (VCO) chip (74LS629), which only puts out a signal when the Enable line is pulled low (0 volts). The signal put out by the VCO is simply a square wave of the frequency determined by an external vibrating crystal. In this case, a 10.000 megahertz crystal was used. This signal was divided by 100 to find hundredths of milliseconds which was the least count of the timer. This was done by feeding the clock signal from the VCO into the Count-Up input of the first Binary-Coded-Decimal (BCD) counter chip (74LS192). The carry signal from this chip was then fed into the Count-Up input of the next 74LS192, with the resulting signals being shown in FIG. 23. Additional 74LS192 chips were attached in the same manner until a count of the ten milliseconds place was achieved. Outputs of the actual number stored in the top four 74LS192 chips were fed into seven segment decoder/driver chips (74LS48) which changed the BCD data to the format required by the seven segment LED display chips. The result was a light beam timer which was accurate to 0.01ms.

Figure 22:
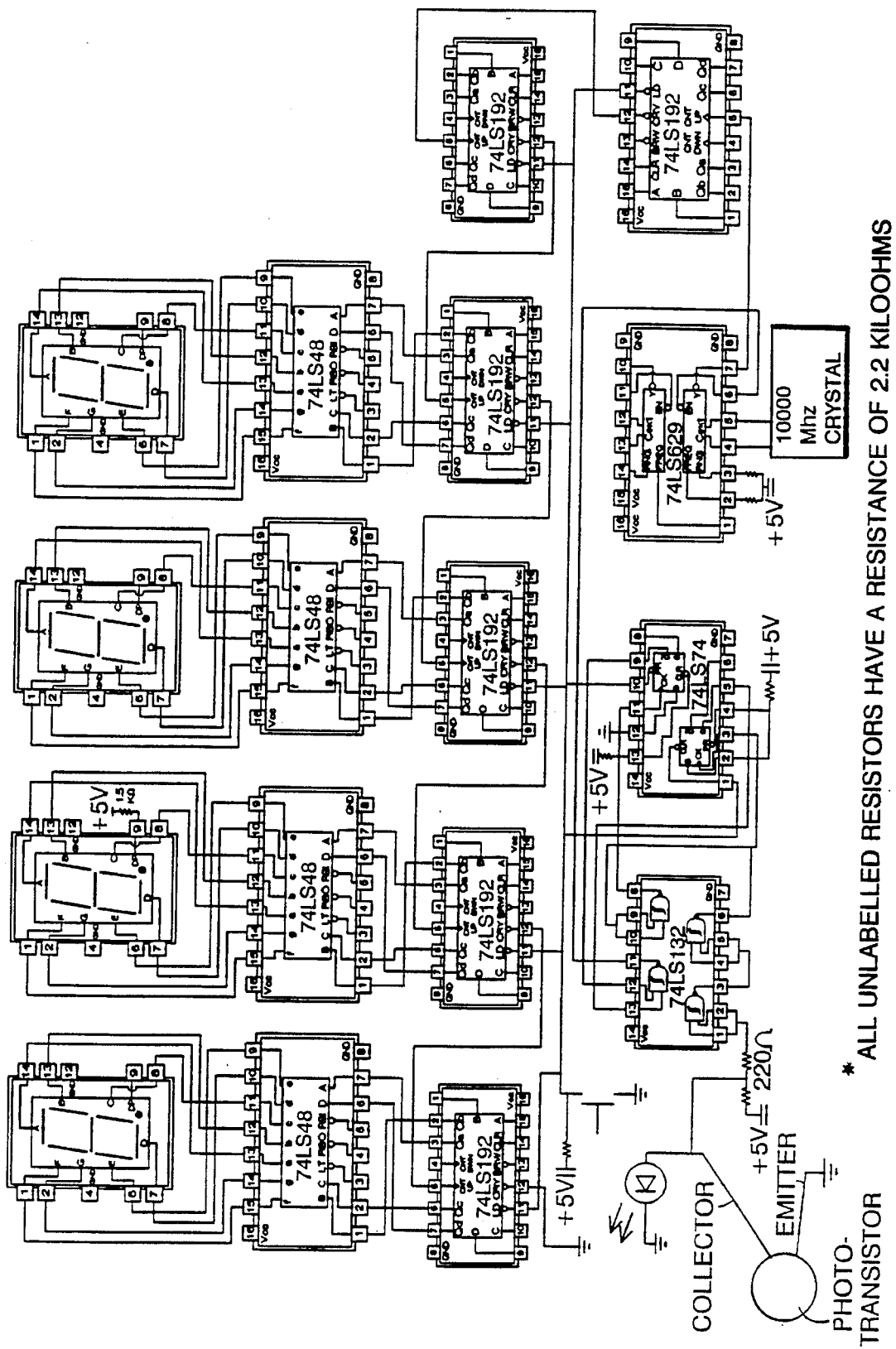
FIG. 22 is a somewhat diagrammatic representation of a timing circuit.

The components used for construction of the timing circuit are listed in Table 5. It was wired as shown in FIG. 22 and as described below. All resistors not labelled in the figure have a resistance value of 2.2 kiloohms. The individual chips are provided power by connecting the pin labelled Vcc on each chip to a positive five volt supply. Two Radio Shack #7805 five volt voltage regulators and two nine volt batteries were used to extend battery life and increase the accuracy of the results. One battery and voltage regulator was used to power the seven segment decoder/drivers (74LS48), because these chips provided power to the display chips and therefore required greater current. The other battery and voltage regulator was used to power the remaining chips, the LED, and the photo transistor. All of the pins marked ground (GND) on each chips were connected to negative terminal of the battery. In addition, the four data input pins (marked A, B, C and D) on all of the counter chips (74LS192) were also connected to ground. This was done so that the value stored in the chips went to zero whenever the push button activated the load operation as discussed above.

TABLE 5

| Timing Circuit Components | | |
|---|---|---|
| Component | Quantity Used | Component Description |
| 74LS132 | 1 | Quadruple 2-Input Positive Nand Schmitt Triggers |
| 74LS74 | 1 | Dual D-Type Positive Edge-Triggered Flip-Flops With Preset and Clear |
| 74LS629 | 1 | Dual Voltage-Controlled Oscillators |
| 74LS192 | 6 | Synchronous 4-Bit Up/Down Binary Coded Decimal (BCD) Counters (Dual Clock and Clear) |

TABLE 5-continued

| Timing Circuit Components | | |
|---|---|---|
| Component | Quantity Used | Component Description |
| 74LS48 | 5 | BCD-to-Seven Segment Decoders/Drivers |
| SK2056 | 5 | Digital Display, Seven Segment, Common Cathode |
| 7805 | 2 | Five Volt Radio Shack Voltage Regulator |
| TXC32 | 1 | 10.000 Megahertz Jim-Pak Oscillating Crystal |
| SK2031 | 1 | Thomson Consumer Electronics, NPN Silicon Photo Transistor |
| — | 6 | 2.2 Kiloohm, 0.5 watt, Electronics Grade Resistors |
| — | 1 | 1.5 Kiloohm, 0.5 watt, Electronics Grade Resistor |
| — | 1 | 220 Ohm, 0.5 watt, Electronics Grade Resistor |
| — | 1 | Radio Shack 276-018 Light Emitting Diode (LED) |
| — | 2 | 9 Volt Batteries |

Once design and construction of the timer circuit were complete, the timer apparatus was set up with the impact mechanism. This was done by first aligning the laser so that the beam (B) hit the hammershank 12 four inches below the pivot point of the hammer assembly. This distance was as close to the head as was possible while assuring that the felt of the hammer head would not disrupt the beam.

Next, the laser was then aligned so that the beam was perpendicular to the trajectory of the hammer. Finally, the laser was moved so that the beam was reestablished when the hammer was 0.1 inch (2.54 mm) away from the impact plate surface after passing through the beam toward impact.

Once the laser was aligned, the photo transistor 28 of the timing circuit was placed in the path of the laser beam on the opposite side of the hammer from the laser source. The photo transistor was then moved to peak the aim, indicated by the LED first going dim and finally going off completely. This places the photo transistor in the path of the laser beam, with the beam striking it perpendicular to its front surface.

Impact Plate Configurations and Construction

In a real piano, the hammer strikes a string, or group of strings, whose diameter is less than the width of the hammer felt. In order to make the conditions of the interface between the piano hammer and the struck surface as real as possible, impact plates were made to simulate the actual piano strings These impact plates 36', 36" and 36'" (FIGS. 24a–24i) were constructed for the appropriate piano hammer. For hammer #1 through hammer #26, the piano strings are unique for each hammer. The rest of the piano hammers can be separated into groups which strike similar string configurations.

The impact plates 36', 36", 36'" were constructed of several pieces, including a disc-shaped impact plate element 54 with a center mounted 10–32 UNC stud 56 (purchased from PCB Piezotronics). For the triple strings (FIGS. 24a–24c), a hexagonal plate 58 with a circular depression cut into the back and three strings 60 were mounted on raised ridges 61 machined on the front surface. The depression was used for centering and attachment of the impact plate discussed above. The three ridges were added to ensure that a fully compressed hammer did not come in contact with the flat surface of the impact plate. Each of the raised ridges was the same height and had a "V" shaped groove machined in its crest to aid in aligning the piano wire that was glued to each. The wire that was used was piano wire which was supplied by Steinway and Sons. Ten impact plates of this type were constructed using piano wire of gages and dimensions shown in Tables 6 and 7. It was determined by measurement that the three strings in the treble notes are the same distance between centers (0.125 inch or 3.16 mm) at the striking point throughout the range of triple strings. Therefore, these impact plates are interchangeable except for the gage of wire that is attached. However, the strings are not exactly parallel.

TABLE 6

Impact Plate Configuration for Specified Hammers

| Hammer Number Configuration | Impact Plate |
|---|---|
| 1–10 | Wound Single String Model |
| 11–26 | Wound Double String Model |
| 27–34 | Triple String 18 Gage Piano Wire |
| 35–46 | Triple String 17 Gage Piano Wire |
| 47–52 | Triple String 16.5 Gage Piano Wire |
| 53–57 | Triple String 16 Gage Piano Wire |
| 58–63 | Triple String 15.5 Gage Piano Wire |
| 64–69 | Triple String 15 Gage Piano Wire |
| 70–74 | Triple String 14.5 Gage Piano Wire |
| 75–78 | Triple String 14 Gage Piano Wire |
| 79–82 | Triple String 13.5 Gage Piano Wire |
| 83–88 | Triple String 13 Gage Piano Wire |

For the copper wound strings that form the single and double strings of the lower notes, a different technique was used for forming the models shown in FIGS. 24g–24h and 24d–24f, respectively. In this case, it was not practical to attach a whole string to the impact plates, and cutting a section of the strings may have resulted in the copper unwinding and the core sliding out, so a silicone mold was made of each string or group of strings, taking care to ensure proper spacing between the double strings. To begin this process, whole strings were inserted into holes drilled in opposite sides, near the bottom, of plastic cups. A silicone rubber compound (RTV21) was poured into the cups until the string was covered to a thickness of approximately 0.125 inch, and the silicone was allowed to harden overnight. It should be noted that the common practice of placing the silicone molds in a vacuum after pouring was not used because placing the silicone in a vacuum would have caused the silicone to flow between the windings of the string making removal difficult and likely tearing the mold.

Once the silicone was hard, the plastic cups were cut off and two cuts were made into the silicone parallel to each string. These cuts created a narrow channel through which the strings could be removed. The double strings 62 (impact plate 36") and single string 64 (impact plate 36''') were then attached upon the respective impact plate elements 54.

TABLE 7

Piano Wire Diameters

| Wire Gage | Wire Diameter |
|---|---|
| 13 | 0.031 inch |
| 13.5 | 0.032 inch |
| 14 | 0.033 inch |
| 14.5 | 0.034 inch |
| 15 | 0.035 inch |
| 15.5 | 0.036 inch |
| 16 | 0.037 inch |
| 16.5 | 0.038 inch |
| 17 | 0.039 inch |
| 18 | 0.041 inch |

Next, two sheets of Mylar (overhead transparency material) were inserted into the silicone perpendicular to the string mold to create ends of the mold approximately one inch apart. For the double strings (FIGS. 24d–24f), the two string channels were connected at either end to allow an epoxy bridge to form at either end and maintain proper spacing between the strings. (Two part HYSOL epoxy was poured into the molds within two hours of removal of the strings to avoid shrinkage of the RTV mold, which can occur over long periods of time.) Once poured, the mold was placed in a vacuum chamber and a vacuum of approximately 1.5 inches Mercury (gage) was applied for ten minutes to draw out the air bubbles created by mixing the epoxy. The mold was then moved to a pressure chamber and a pressure of 20 pounds per square inch gage was held until the epoxy was hard to increase the density of the model and to collapse any residual air bubbles. The result was a strong, dense model of the string or strings which was then attached to disc shaped impact plates purchased from PCB Piezotronics.

Figure 25:
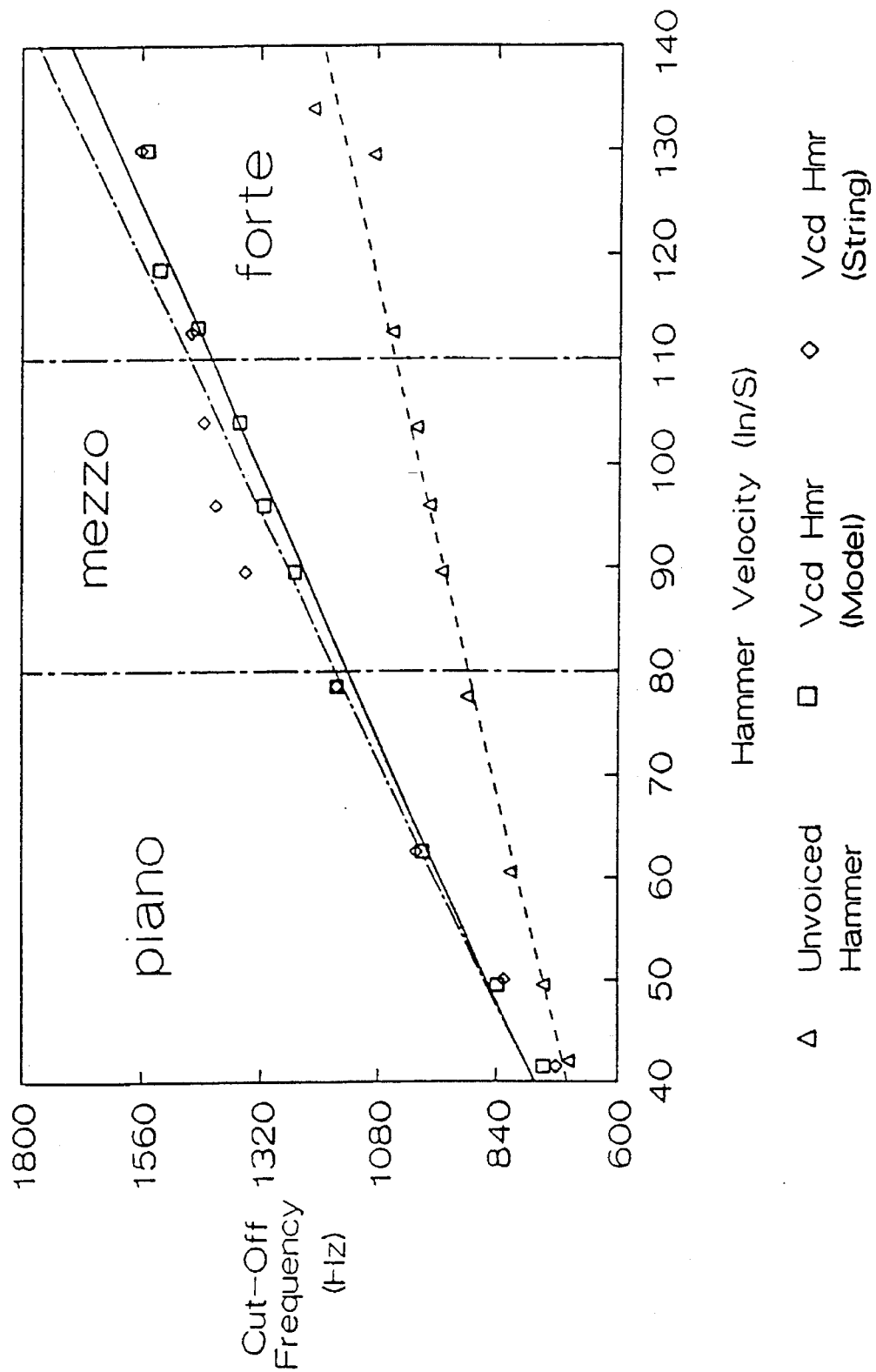
FIG. 25 is a plot of a hammer #1 striking a model versus a string.

In order to ensure the acceptability of this solution, string #1 was soldered to an impact plate and tested. The results of this test can be seen in FIG. 25 which shows the difference between a voiced piano hammer being struck against the real string as well as the epoxy model as compared to the unvoiced hammer being struck against the model. From this graph, it can be seen that there is very little difference between the curves for the voiced hammer struck against the string and the voiced hammer struck against the epoxy model. However, there is a large difference between these two curves and that of the unvoiced hammer. Therefore, the use of an epoxy model was shown to be an acceptable method for the experiment.

Statistical Energy Quantities Used for Vibrational and Acoustical Analysis

The Fourier Transform of some continuous function is defined as:

$$F(\omega) = \frac{1}{2\pi} \int_{T=-\infty}^{\infty} F(\tau) e^{-i\omega \tau} d\tau.$$

The Fourier Transform for a set of discrete data points known as the Discrete Fourier Transform (D.F.T.) and is defined as:

$$f_N(\omega) = \frac{1}{N} \sum_{k=0}^{N-1} f(\tau_k) e^{-i\omega \tau_k}.$$

When Fourier Transforms are performed on data or functions which have time as the independent variable, the result is new data or functions which have frequency as the independent variable.

Now that the Fourier Transform has been defined, Power Spectrum can be defined as the Fourier Transform of the signal, which is a complex number, times its complex conjugate, or $f_N(\omega)f_N(\omega)^*$ where the * denotes the complex conjugate. The Power Spectral Density can also be defined now as the Power Spectrum of some discrete data divided by the bandwidth for that data, or $f_N(\omega)f_N(\omega)^*/\Delta\omega$. Therefore, for continuous data, the Power Spectrum is simply the integral from zero to infinity of the Power Spectral Density with respect to frequency. It should be noted that the units for Power Spectrum and Power Spectral Density in accordance with the above definitions are some amplitude squared and that amplitude squared divided by Hertz, respectively.

Another type of spectrum is the Shock Spectrum. This spectrum shows the magnitude of the response peaks as a function of the natural frequency of the responding system, at various values of the fraction of critical damping.

The above definitions are the commonly accepted definitions for those terms. Hewlett-Packard defines the Power Spectrum basically the same way and also defines several other types of Spectra which are used for data display on the HP 3562A. The Power Spectrum display on the HP 3562A is defined as is generally accepted, except that it is presented with a decibel representation for the signal amplitude, with the actual units displayed being decibel volts squared. Another type of spectrum which is used on the HP 3562A is called the Linear Spectrum which is simply the FFT of a given signal. Therefore, what is displayed for this Spectrum is again a decibel representation of the magnitude of the Spectrum, with the actual units being decibel volts. However, the phase data is stored in the HP 3562A for later use if it becomes desirable. For the purposes of this experimentation, the phase data was not necessary and would have wasted space on the storage discs so the Power Spectrum measurement was used.

The major stumbling block to widespread use of Fourier Transforms on data had always been the number of calculations required was very large. For the calculation of a given $f_N(\alpha)$, on the order of $N^2[\Theta(N^2)]$ operations of multiplication and addition had to be performed. However, in 1965 James Cooley and John Tukey published a paper showing that if N consecutive $f_N(\alpha)$'s are to be calculated, the operations could be condensed to require only $\Theta(N\log N)$ operations. For the case of the HP 3562A, which collects 2048 data points in the Linear Resolution Mode, this translates to thousands of operations in lieu of millions of operations for each record.

Other Embodiments

Figure 26A:
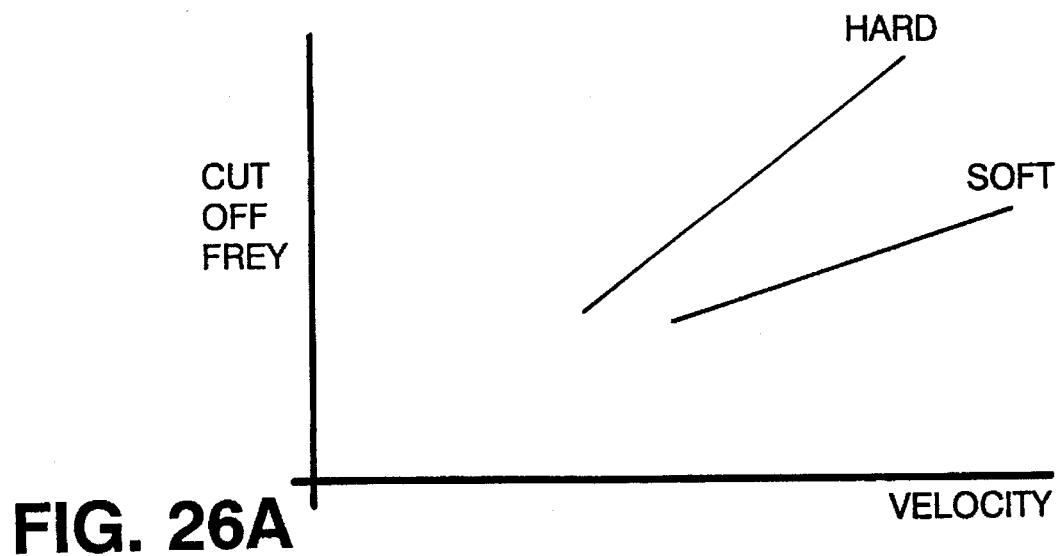
FIGS. 26 and 26A are schematic plots of velocity versus force and cut-off frequency, respectively, for an alternative method of the invention.
Figure 26:
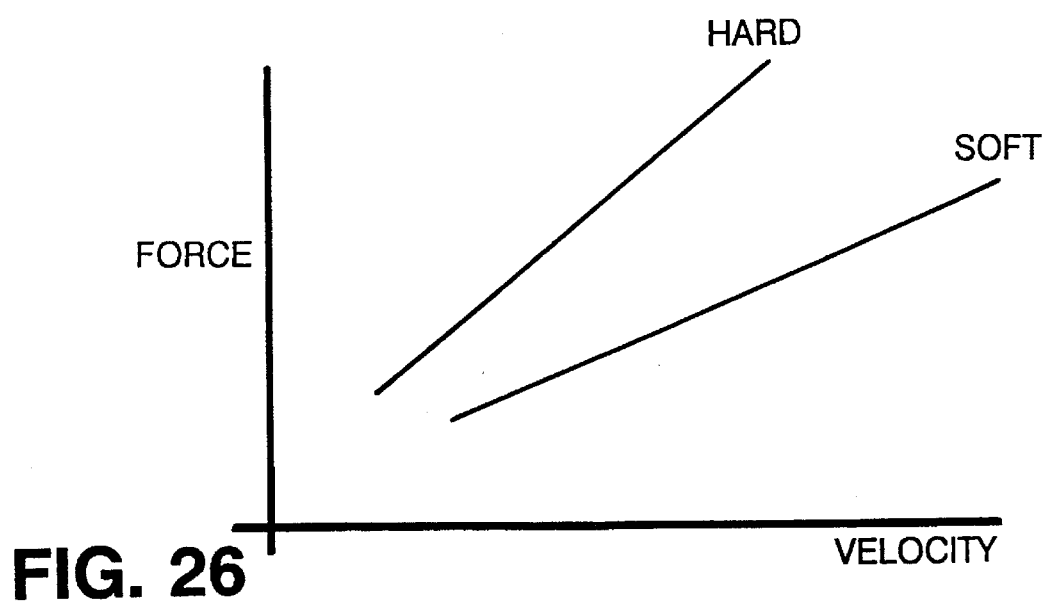

Other embodiments of the invention are within the following claims. For example, another means for determining hardness of a piano hammer is to measure the slope of the hammer force versus hammer velocity or (equivalently) hammer frequency cut-off versus velocity. As seen schematically in FIGS. 26 and 26A, the harder the hammer, the higher the slope. A procedure for testing might involve releasing the piano hammer so as to impart, e.g., four different velocities and measure the force, then compute the average slope, thus to avoid taking FFTs.

The method of the invention may be expanded for use in general dynamic hardness testing of soft materials. Since soft materials are often used as vibrational isolators and dampers, the frequency data of the impact of a given material will also prove useful in determination of the material to be used.

Figure 27:
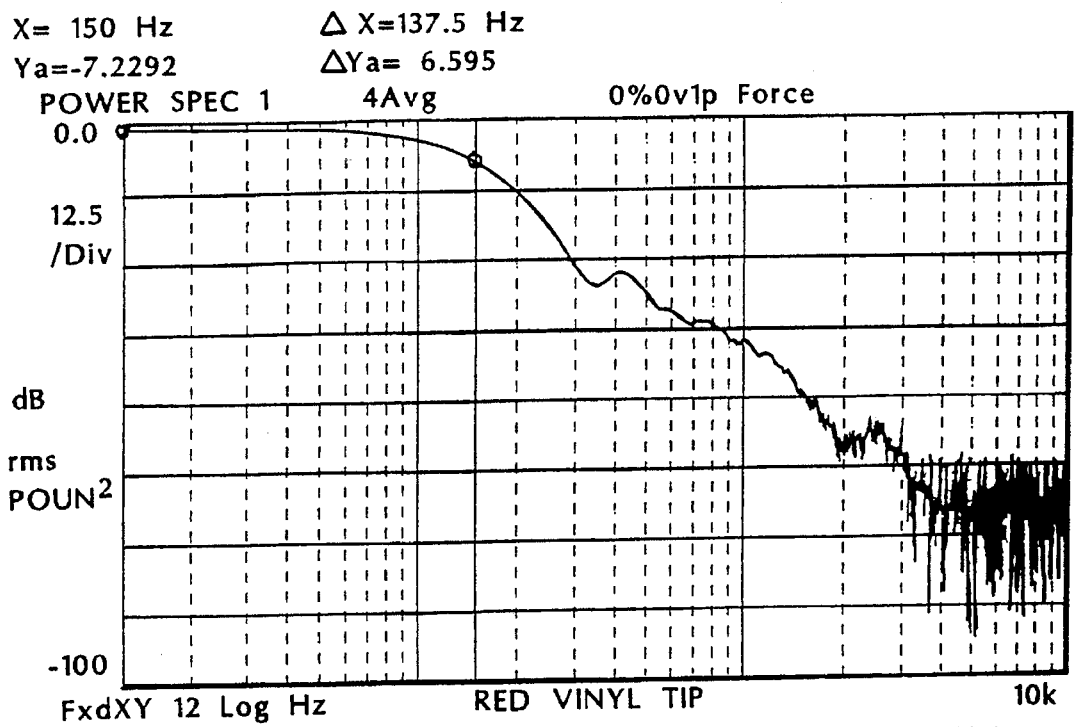
FIG. 27 is a plot of Power Spectra data for a red vinyl tip.
Figure 27A:
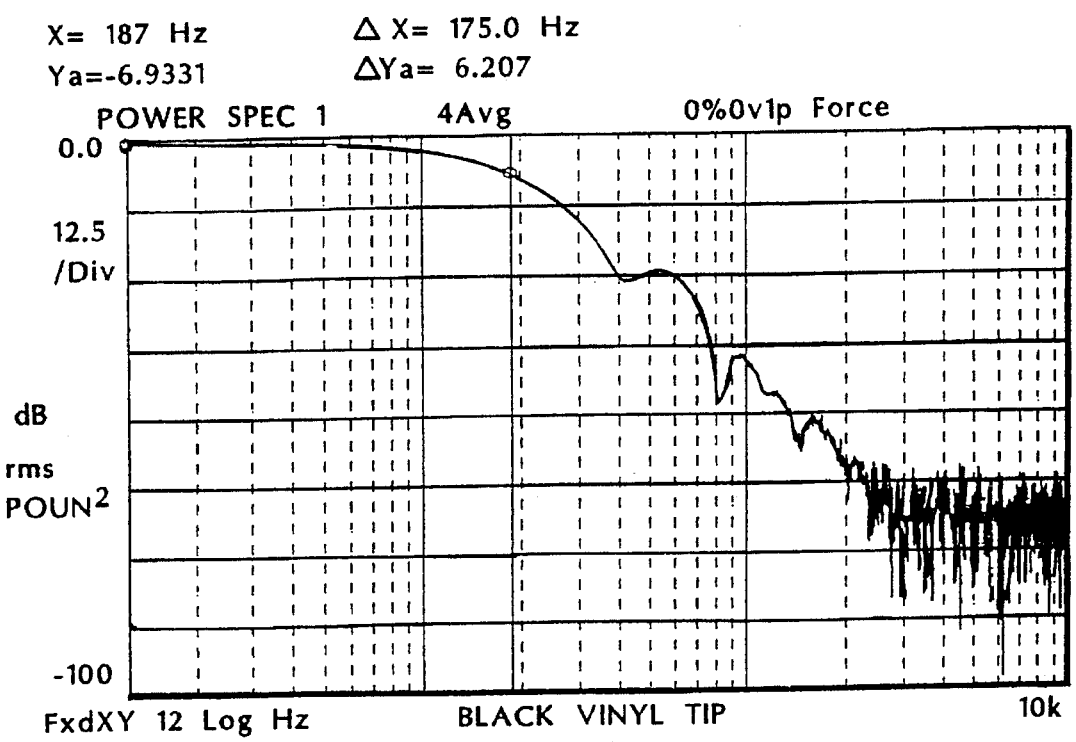
FIG. 27A is a plot of Power Spectra data for a black vinyl tip.
Figure 27B:
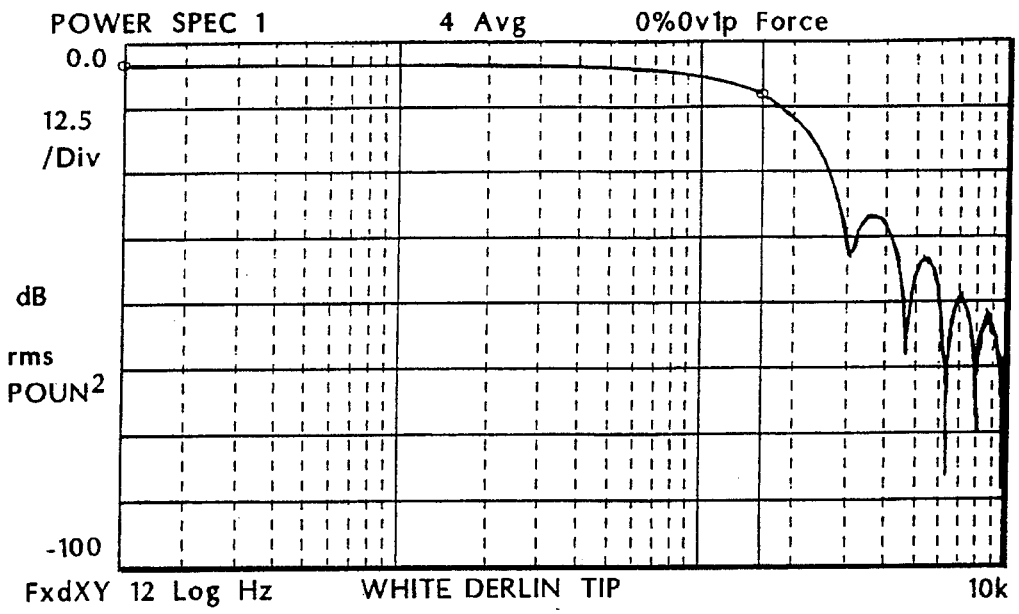
FIG. 27B is a plot of Power Spectra data for a white Delrin tip.

Several additional tests were performed for illustration of the usefulness of this procedure. These tests were performed using a PCB Piezotronics Model 086B03 impulse hammer commonly used for modal testing. This hammer was chosen because it provided a constant mass and interchangeable tips for the striking surface. The three tips used were a red vinyl (super soft) tip, a black vinyl (soft) tip, and a white Delrin (medium) tip with the Power Spectrum results shown in FIGS. 27, 27A and 27B, respectively. As can be seen from examining these figures, the cut-off frequency for the red tip is 150 Hertz, for the black tip is 187 Hertz and for the white tip is 1575 Hertz. Clear distinction is seen between the three tips, even though the testing was performed without tight control over impact velocity because of the illustrative nature of the tests.

Figure 28:
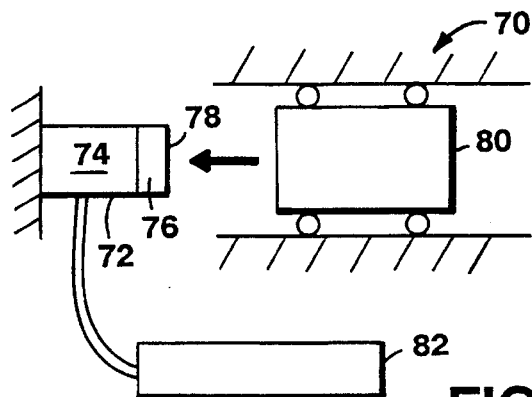
FIGS. 28 and 28A are somewhat schematic diagrams of alternative embodiments of testing apparatus of the invention.

According to another embodiment of the invention, in an apparatus 70, shown in FIG. 28, an axial force measuring load cell 72 is attached to a large (effectively infinite) mass 74. The load cell 72 has a special head 76 with surface 78 for the mobile, felt-tipped piano hammer 80 to impact in the direction F. The load cell output is analyzed by analyzer 82.

Figure 28A:
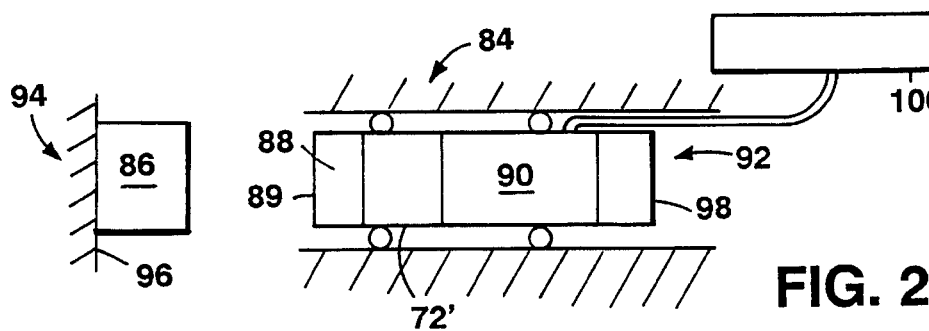

In an alternative system 84, shown in FIG. 28A, useful for the generic measurement of hardness of any material 86 (including, e.g., felts, rubber, plastic, composites, metal, wood, woven fabrics, etc.), has the load cell 72', with a tip 88 having a surface 89 that is harder than the material 86 being impacted, attached to a mobile inertial mass 90 such as a modal analysis hammer or other means to deliver a tipped/instrumented mobile inertial mass system 92 impulsively to the material 86 being tested. The mobile element 92 would impact the stationary material 86 placed against a large (effectively infinite) mass 94 whose surface 96 is also sufficiently harder than the material 86 being tested. In addition, an in-line accelerometer 98 could be attached to the inertial mass. The output of all sensors is analyzed by analyzer 100. Similar cut-off frequencies could be determined from the acceleration (or from the velocity or displacement, as discussed below). Also, the accelerance (acceleration/force) or its reciprocal, the apparent mass; the mobility (velocity/force) or its reciprocal, the impedance; or the receptance (displacement/force) or its reciprocal, the dynamic stiffness, could be measured and/or computed. Any number of these quantities in the time domain or frequency domain could be used as a measure of hardness of any material including metals, but especially soft or limp materials. Since the acceleration is the first derivative of the velocity and the second derivative of the displacement, these relations (or their integral equivalents) can be used to obtain any derived quantity from their respective measured primitives.

In another embodiment, the accelerometer 98 can be replaced by a mobile in-line velocimeter or a mobile in-line displacement sensor.

Figure 29:
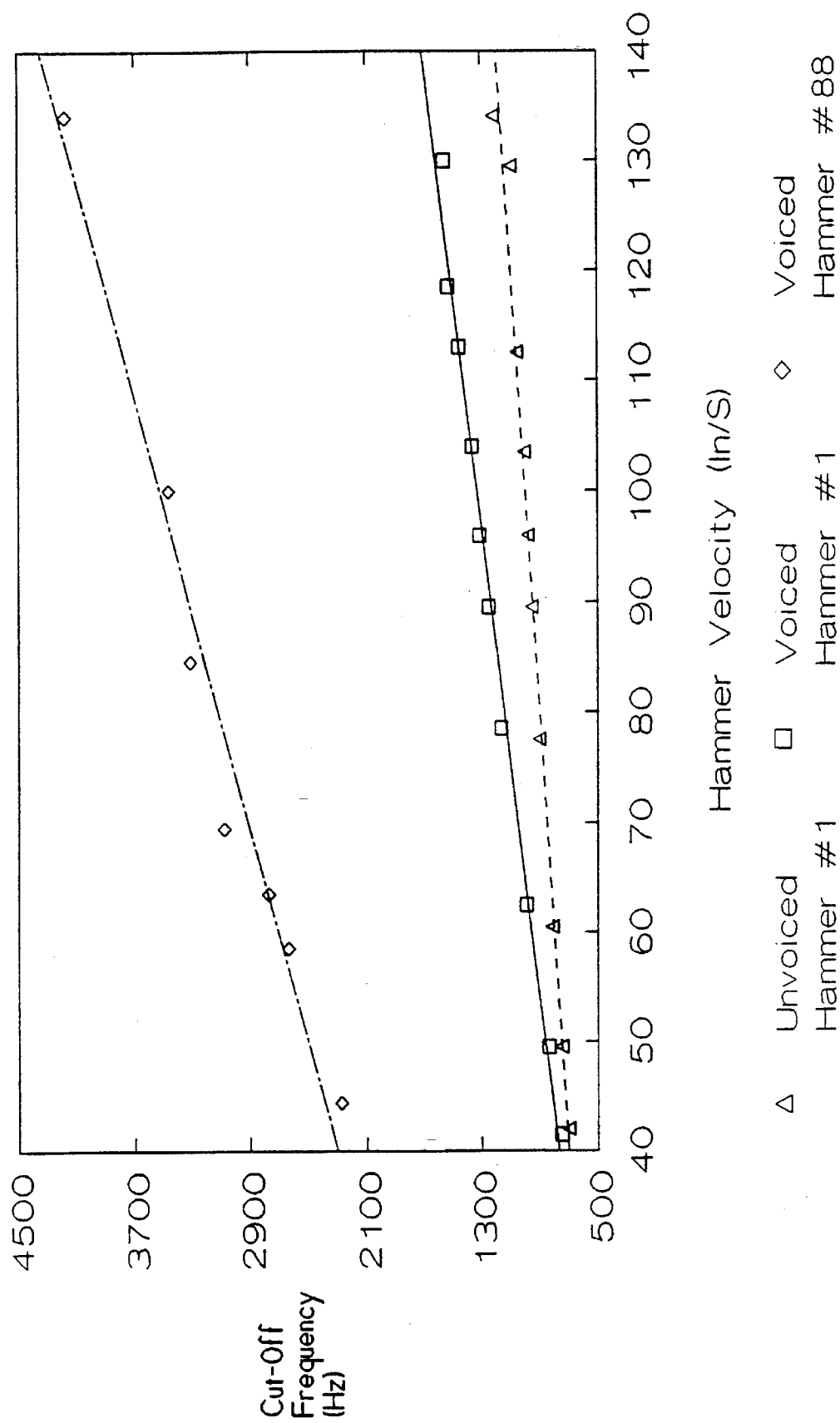
FIG. 29 is a plot of cut-off frequencies of samples.

Another method of interpreting the data and differentiating between various materials is to test a given specimen at several different initial velocities. When the cut-off frequencies are plotted versus the velocity, as can be seen in FIG. 29, which shows data for three piano hammers of varying hardness, the slope of the best fit line through the data will characterize the material in question. As can be seen in this figure, the slope for a harder material (piano hammer #88) is 20.42 hertz per inch per second, while the slope for a softer material (unvoiced piano hammer #1) is only 4.875 hertz per inch per second.

Figure 30:
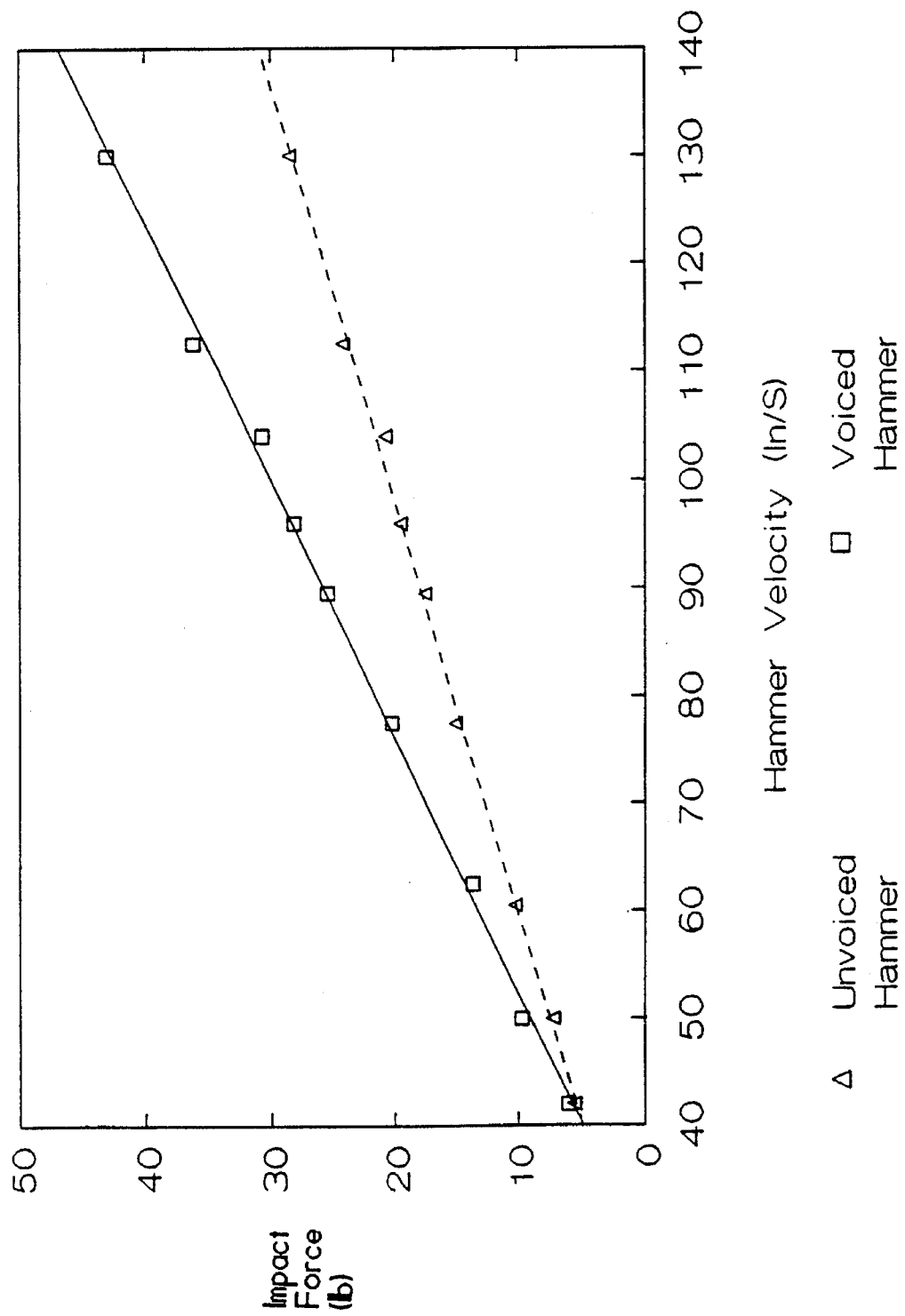
FIG. 30 is plot of impact force data for a hammer

A twist on the above discussion is to examine the plots of peak force versus velocity as shown in FIG. 30 for piano hammer #1. Measurement of the slope of the linear regression curve of the data may also be used as the regulation standard. This figure shows a slope of 0.2617 pound per inch per second for an unvoiced hammer and 0.4205 pound per inch per second for a voiced hammer. The predominant benefit of this alternative is that an FFT analyzer is not necessary, since it may only be required to measure this force versus velocity slope to ascertain the material hardness, or degree of piano hammer regulation.

The method and apparatus of the invention may be used for development of testing procedures and apparatus, including establishment of a scale, of a standard dynamic hardness testing method similar, and as a possible alternative, to, e.g., ASTM D2240-86, *Standard Test Method for Rubber Property-Durometer Hardness*, used for Shore Durometer hardness testing.

What is claimed is:

1. A method for measuring the dynamic hardness of an elastic material, comprising causing impact between a test element of the elastic material and an impact surface, measuring a striking force between the test element and the impact surface, measuring a relative impact velocity between the test element and the impact surface, and analyzing both the striking force and the impact velocity to measure the dynamic hardness of the elastic material.

2. The method of claim 1 wherein said analyzing further comprises the step of determining the slope of the striking force versus the impact velocity.

3. The method of claim 2 wherein the impact of said test element with said impact surface is characterized by a power spectrum cut-off frequency, said method comprising the further step of determining the power spectrum cut-off frequency for the impact of said test element with said impact surface, and determining during said analyzing a slope of the cut-off frequency versus the impact velocity.

4. A method for measuring the dynamic hardness of an elastic material, comprising:

causing impact between a test element of the elastic material and an impact surface, wherein said impact of the test element with said impact surface is characterized by a power spectrum cut-off frequency;

measuring the relative impact velocity between the test element and the impact surface;

determining the power spectrum cut-off frequency for the impact of the test element with the impact surface; and, determining the slope of the power spectrum cut-off frequency versus impact velocity to measure the dynamic hardness of the elastic material.

* * * * *